United States Patent [19]
Humphries

[11] Patent Number: 5,804,177
[45] Date of Patent: Sep. 8, 1998

[54] METHOD OF USING CD24 AS A CELL MARKER

[76] Inventor: R. Keith Humphries, 7625 Borden Street, Vancouver, British Columbia, Canada, V5P 3CP

[21] Appl. No.: 848,252

[22] Filed: Apr. 29, 1997

Related U.S. Application Data

[63] Continuation of Ser. No. 538,052, Oct. 2, 1995, abandoned, which is a continuation of Ser. No. 151,672, Nov. 15, 1993, abandoned.

[51] Int. Cl.$^6$ .............................. A61K 49/00; C12Q 1/68; C12Q 1/70; C12N 15/86
[52] U.S. Cl. ................................ 424/93.2; 435/5; 435/6; 435/7.1; 435/7.2; 435/7.21; 435/320.1; 435/372
[58] Field of Search .......................... 435/5, 6, 7.1, 7.2, 435/7.21, 320.1, 372, 325, 355; 424/93.2, 93.6

[56] References Cited

PUBLICATIONS

Koz et al. "Expression Cloning of a cDNA Encoding M1/69–J11d Heat Stable Antigens", J. of Immunol., vol. 145, No. 6, Sep. 15, 1990, pp. 1952–1959.
Pawlink et al. "The CD24 Cell Surface Antigen as a Dominant Selectable Marker in Retroviral Mediated Gene Transfer" J. Cell. Biochem., Supplement 17E, 1993, Abstract S210.
Spangrude et al., Science, vol. 241, pp. 58–62, 1988.
Ploemacher, R.E. & Brons, R.H.C., Exp. Hematol., vol. 17, pp. 263–266, 1989.
Yang et al. MC Biol. 7:3923, 1987.
Green et al., Proc. Natl. Acad. Sci. USA 88:8475, 1991.
Strair, R.K. et al., Nucleic Acids Res. 18:4759, 1990.
Kang et al., Proc. Natl. Acad. Sci. USA 87:9803, 1990.
Korman et al., Proc. Natl. Acad. Sci. USA 84:2150, 1987.
Emery et al., Transplantation Proceedings 24:468, 1992.
Sykes et al., Transplantation 55:197, 1993.
Strair et. al., J. Virology 62:4756, 1988.
Olsen et al., Nucleic Acids Research 21:633, 1993.
Choi et al., Proc. Natl. Acad. Sci. 88:7386, 1991.
Kay, R. et al, 1991, J. Immunol. 147:1412.
Nabel et al., JACC, 17:189B, 1991.
Capel et al., Blood, 75:2267, 1990.

*Primary Examiner*—David Guzo
*Attorney, Agent, or Firm*—Bereskin & Parr

[57] ABSTRACT

A method of marking a cell involving introducing into the cell a nucleotide sequence encoding a cell surface protein and having substantial homology to the nucleotide sequence encoding CD24, and expressing the cell surface protein on the cell.

10 Claims, 11 Drawing Sheets

Uninfected Ba/F3

CD24 virus infected Ba/F3

Log fluorescence

Uninfected BM

CD24 virus infected BM

Log fluorescence

Uninfected BM

CD24 virus infected BM

Log fluorescence

FIGURE 7A
FIGURE 7B
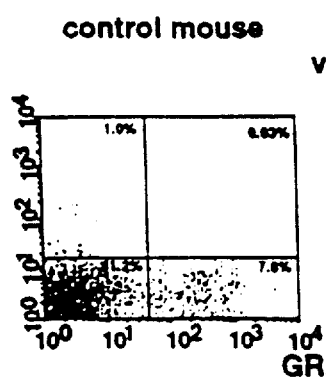
control mouse
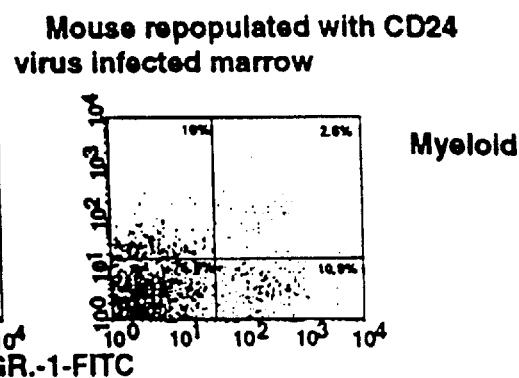
Mouse repopulated with CD24 virus infected marrow
Myeloid
GR.-1-FITC
FIGURE 7C
FIGURE 7D
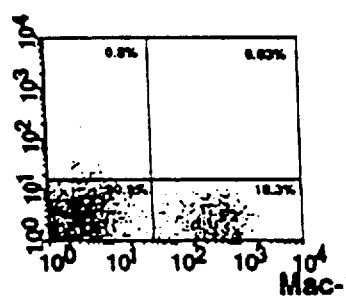
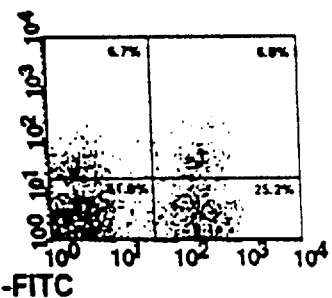
Mac-1-FITC
FIGURE 7E
FIGURE 7F
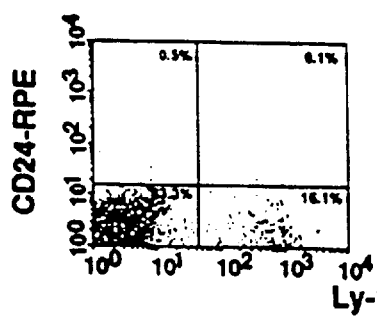
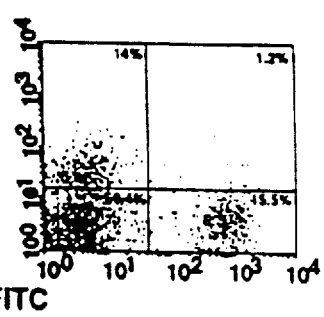
Lymphoid
CD24-RPE
Ly-1-FITC

B220-FITC

Erythroid (RBC)

Ly5.1-FITC

FIGURE 8

```
CGGTTCTCCAAGCACCCAGCATCCTGCTAGACGCGCCGCCGCCACCGACGGAGGGACATGGGCAGAGCAATGTGGCCAGGTCTCGGGCTCGGGCTGCTGGCACTGCT  112
                                               M  G  R  A  H  V  A  R  L  G  L  G  L  L  L  A  L  L
CCTACCCACCGCAGATTTATTCCAGTGAAACAACAACTGGAACTTCAAGTAACTCCTCCCAGAGTACTTCCAACTCTGGGTTGGCCCAAATCCAACTAATGCCACCACCAAG  224
  L  P  T  Q  I  Y  S  S  E  T  T  T  G  T  S  N  S  Q  S  T  S  N  S  G  L  A  P  N  P  T  N  A  T  T  K
GCGGTGGTGGCCCTGCAGTCAACAGCCAGTCTCTTCGTGGTCTCTCTGCATCTCTACTCTTAAGAGACTCAGGCCAAGAAGTCTCTAAATTTCCCCA  336
  A  A  G  A  L  Q  S  T  A  S  L  F  V  V  S  L  L  H  L  Y  S
TCTTCTAAACCCAATCCAATCCAAATGGCGTCTGGAAGTCAATGTGGCCAAGGAAAAACAGTCTTCATCGAATCTACTAATTCCACACCTTTTATTGACACAGAAATGTTGAGAA  448
TCCCAAATTTGATTTGAAGAACATGTGAGAGGTTTGACTAGAGTTGACTGATGCAATATTAAATCTGTGGAGTTTCATGTACAAGATGAAGGAGAGCAACATCCAAA  560
ATAGTTAAGACATGATTTCCTTGCAGTGAATGTGGCTTGAGAAATATGGACACTTAATACTACCTTAAGAATAGAATAAAGGATTGTGAATGGAGATTCAGTTT  672
TCATTTGGTGCTTAATTCTATAAGCGTATAAACAGGTAATATAAAAGCTTCCATGATTCTATTTATATGTACATGAAGGAACTTCCAGTGTTACTGTAATTCCTCAAC  784
GTATGTTTCGACGGCACTATTGACCTTTTAATTTAATGCCGATAATCTAGAGTTTTACATTGTTGAGCTATTGCTGTTCTCTTGGAACTGAACTCACTTCCTCCTGAGGCTTG  896
GATTTGACATTGCATTGTAGGCATTGCCGATCATCCTGTTTCCATTCAACAGAGACATTCAGTTCAACAAGATTCCAAAGAGTAGAATTGCATTGACCACGACTAATTC  1008
TGAGTCAAATGCTTTTCCTATCACCTGTTTCCATTCAACAGAGACTCACTTTGTCGCCCAGGCCAGTGGTGCAGTGCTAATTTTGTAATTTTAGTAGAGACAGGGTTTCACCATGTTGCCCAGGCTGGT  1120
AAATGCTTTTATTATTATTTTATTTTTAGACAGTCTGGGATTACAGGCACCTCCCACATGCCCGGCCTCCCAAAGTGCTGGGATTACAGGCGTGAGCCCGCCACCATGCCCGGCCATCAAAATGCTTTTATTCTGCATATGT  1232
TTCCTGCCTTGCCTCAGCCTCGACCTGATCGACCCGGCCTCAGGTGATCCAAGTAGCTCCACCGCCTCGGGATTACAGGCGTGGATTACAGGCTTGAAGGCAGAATGATCTGTTTGAAGGCAAATCTGTTTGAAGGCAGAATTGCAAATCTGAAATTAAGGAGTCAAATCAAGTATTTGGG  1344
TTGAATACTTTTACAATTTTAAAAAATGATCTGTTTGAAGGCAAATCTGTTTGAAGGCAAATTGCAAATCTTGTTTCTGTATATACATTTTTCTTTAAAAACAACTATGGATCAGAATAGCCACATTTAGAA  1456
AAGTGAAGACTGAAGCTAATTGCATAAATTGCATAAATTGCATAAAAACTTTTATACTCTTTCTGTATATACATTTTTCTTTAAAAACAACTATGGATCAGAATAGCCACATTTAGAA  1568
CACTTTTGTTATCAGTCAATATTTTAGATAGTTAGAACCTGTCTGATTCTGCAGTAATCTTTTACAGTGGGCTAAAATCTTTTGCAGTAATCTTTTACAGTGGGCTGAACCTGTCTGATTCTGCAGTAATCTTTTACAGTGGGCTGACACAGACATAAACCT  1680
TTTTAAAAATAGACACTCC 1811
```

FIGURE 9A

```
   1 CCCCGCGCGAGCTTAGCAGATCTCCACTTACCGAACATCTAGAGAGTCGCGCCGCGCGCC   60
  61 GACGGAGCGGACATGGGCAGAGCGATGGTGGCCAGGCTAGGGCTGGGGTTGCTGCTTCTG  120
                M   G   R   A   M   V   A   R   L   G   L   G   L   L   L   L
 121 GCACTGCTCCTACCCACGCAGATTTACTGCAACCAAACATCTGTTGCACCGTTTCCCGGT  180
      A   L   L   L   P   T   Q   I   Y   C   N   Q   T   S   V   A   P   F   P   G
 181 AACCAGAATATTTCTGCTTCCCCAAATCCAAGTAACGCTACCACCAGAGGGGGTGGCAGC  240
      N   Q   N   I   S   A   S   P   N   P   S   N   A   T   T   R   G   G   S
 241 TCCCTGCAGTCCACAGCTGGTCTCCTGGCTCTCTCTCTCTCTTCTACATCTCTACTGT    300
      S   L   Q   S   T   A   G   L   L   A   L   S   L   S   L   L   H   L   Y   C
 301 TAGAGACTCAGGCCAGGAAACGTCTCTACTTCCCCATCTTCTACACCTACCCCAAATGGC  360

361 AACCACAAGTCCAATGTGATCAGGAAGAAACAGGTCCACCTCGAATTGGCTGTTACCATA  420
 421 TCTCAACAGAAAACACGGAGAATTCGAAATTCGACGGGATTAAAGGACGCGTGAAAGGTT  480
 481 TGAGAGAAGAGAGATGCCGCTATTGAATCTGCTGGAGTTTTACATCCCAAGATGAAGACA  540
 541 GCATTCAGAATTGATGTGATTTCCTTGAATCGTGGCTTAGGAAATGTGGACACTTAAAAC  600
 601 TCTCACTTGAAATTGGGCACAGGTTTGATGTAGAGATAAGGACGGGGTGCGGAATGGAGA  660
 661 CCCATTTTGTCATTGATTCATCTGACCGATAAGGCCATAGTGCAGTTAGGTGATATTCGA  720
 721 AAGCTTCTTTGATGCTCTTTATGTATATGTTGGAAGGAACTACCAGGCGTTGCTTTAAAT  780
 781 TCCCAATGTGTTGTTTCGTTACTACTAATTTAATACCGTAAGCTCTAGGTAAAGTTCCAT  840
 841 GTTGTTGAACTCTGACTGTTCTCTTTGGAATTGAACCTTTTGCATCCTCCTCCTGTGGCT  900
 901 TTAGGTCTGACATTGTATTTGACCTTTACTAGTAATTAACATGTGCCAGGCAATGGTGGA  960
 961 TTGGAACCCATCCCCAAGTCCAGCCACCACTGAATAAATCTGATTTCAAAAGTCAAACAG 1020
1021 TAGACATTTCCCATTGTCGTTTCTCACTCACCACAAGCACCAAATTCACTAGAGTACACT 1080
1081 GGTTCCAGAGAGCAGAATCATGTTGGCCTTGGCTAATTTCAAAATGCTGTCTTTTACTTT 1140
1141 GGTATATGTTGAGGGCTTTTCATAATTTAAAGTGTGTTCTGTTAGCAAGGCAAAAATTAT 1200
1201 GAGTCTTAATTCTACAGGCAAATATGCAAAGGAGCCAAAACTGTAAACCCAGCATTTGGG 1260
1261 ATGTGAAGACTGGAAGCTAACTCTCATTGAATTCACAAAGTCTTTTATACAATTTCTGTA 1320
1321 CATACTTTTTTTTTTTTAAGAGAAAAACAAACGGTGGATCAGAATAGCCACGTTTGGAA  1380
1381 TACTTTGGTTATCCATTCATATTTTAGATAGTTATTGGTCCTGTGCCTGAAAGGGGCT   1440
1441 TGGTTCTACCGTAAGTTTTTCCAATTTCCTTGATATACACATACCTTCTAAAACCTAGAC 1500
1501 ATTTCCTGAAAAAAATCTTTTGTTCGCATGGTCACACACTGATGCTTACCCGTACAGTAG 1560
1561 TCTTGATAACCAGAGTCATTTTCTCCATCTTTAGAAACCTTCCTGGAAGAAGGAGAGCTC 1620
1621 ACAGACCCGAAGCTACTGTGTGTGTGAATGAACACTCCCCTTGCCTCACACCTGAATGCT 1680
1681 GTACATCTATTTGATTGTAAATTGTGTTTGTGTATTTATGCTTTGATTCATAGTAACTTC 1740
1741 TCATGTTATGGAATTGATTTGCATTGAACACAAACTGTAAATAAAGAAAGAAATGGCGG  1800
```

OPEN READING FRAMES OF M1/69 cDNA

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
    ( A ) LENGTH: 1811 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: Homo sapiens ( v i i ) IMMEDIATE SOURCE:
    ( A ) LIBRARY: Human
    ( B ) CLONE: Signal Transductor CD24

( i x ) FEATURE:
    ( A ) NAME/KEY: sig_peptide
    ( B ) LOCATION: 57..134

( i x ) FEATURE:
    ( A ) NAME/KEY: mat_peptide
    ( B ) LOCATION: 135..296

( i x ) FEATURE:
    ( A ) NAME/KEY: CDS
    ( B ) LOCATION: 57..299

( x i ) SEQUENCE DESCRIPTION: SEQ ID NO:1:

```
CGGTTCTCCA  AGCACCCAGC  ATCCTGCTAG  ACGCGCCGCG  CACCGACGGA  GGGGAC                   56

ATG  GGC  AGA  GCA  ATG  GTG  GCC  AGG  CTC  GGG  CTG  GGG  CTG  CTG  CTG  CTG      104
Met  Gly  Arg  Ala  Met  Val  Ala  Arg  Leu  Gly  Leu  Gly  Leu  Leu  Leu  Leu
-26  -25                 -20                              -15

GCA  CTG  CTC  CTA  CCC  ACG  CAG  ATT  TAT  TCC  AGT  GAA  ACA  ACA  ACT  GGA      152
Ala  Leu  Leu  Leu  Pro  Thr  Gln  Ile  Tyr  Ser  Ser  Glu  Thr  Thr  Thr  Gly
-10                        -5                    1                        5

ACT  TCA  AGT  AAC  TCC  TCC  CAG  AGT  ACT  TCC  AAC  TCT  GGG  TTG  GCC  CCA      200
Thr  Ser  Ser  Asn  Ser  Ser  Gln  Ser  Thr  Ser  Asn  Ser  Gly  Leu  Ala  Pro
                10                        15                        20

AAT  CCA  ACT  AAT  GCC  ACC  ACC  AAG  GCG  GCT  GGT  GGT  GCC  CTG  CAG  TCA      248
Asn  Pro  Thr  Asn  Ala  Thr  Thr  Lys  Ala  Ala  Gly  Gly  Ala  Leu  Gln  Ser
          25                        30                        35

ACA  GCC  AGT  CTC  TTC  GTG  GTC  TCA  CTC  TCT  CTT  CTG  CAT  CTC  TAC  TCT      296
Thr  Ala  Ser  Leu  Phe  Val  Val  Ser  Leu  Ser  Leu  Leu  His  Leu  Tyr  Ser
     40                        45                        50

TAAGAGACTC  AGGCCAAGAA  ACGTCTTCTA  AATTTCCCCA  TCTTCTAAAC  CCAATCCAAA              356

TGGCGTCTGG  AAGTCCAATG  TGGCAAGGAA  AAACAGGTCT  TCATCGAATC  TACTAATTCC              416

ACACCTTTTA  TTGACACAGA  AAATGTTGAG  AATCCCAAAT  TTGATTGATT  TGAAGAACAT              476

GTGAGAGGTT  TGACTAGATG  ATGGATGCCA  ATATTAAATC  TGCTGGAGTT  TCATGTACAA              536

GATGAAGGAG  AGGCAACATC  CAAAATAGTT  AAGACATGAT  TTCCTTGAAT  GTGGCTTGAG              596

AAATATGGAC  ACTTAATACT  ACCTTGAAAA  TAAGAATAGA  AATAAAGGAT  GGGATTGTGG              656

AATGGAGATT  CAGTTTTCAT  TTGGTGCTTA  ATTCTATAAG  CGTATAAACA  GGTAATATAA              716

AAAGCTTCCA  TGATTCTATT  TATATGTACA  TGAGAAGGAA  CTTCCAGGTG  TTACTGTAAT              776

TCCTCAACGT  ATTGTTTCGA  CGGCACTAAT  TTAATGCCGA  TATACTCTAG  ATGAAGTTTT              836

ACATTGTTGA  GCTATTGCTG  TTCTCTTGGG  AACTGAACTC  ACTTTCCTCC  TGAGGCTTTG              896
```

```
GATTTGACAT TGCATTTGAC CTTTTATGTA GTAATTGACA TGTGCCAGGG CAATGATGAA      956

TGAGAATCTA CCCCAGATCC AAGCATCCTG AGCAACTCTT GATTATCCAT ATTGAGTCAA     1016

ATGGTAGGCA TTTCCTATCA CCTGTTTCCA TTCAACAAGA GCACTACATT CATTTAGCTA     1076

AACGGATTCC AAAGAGTAGA ATTGCATTGA CCACGACTAA TTTCAAAATG CTTTTTATTA     1136

TTATTATTTT TTAGACAGTC TCACTTTGTC GCCCAGGCCG GAGTGCAGTG GTGCGATCTC     1196

AGATCAGTGT ACCATTTGCC TCCCGGGCTC AAGCGATTCT CCTGCCTCAG CCTCCCAAGT     1256

AGCTGGGATT ACAGGCACCT GCCACCATGC CCGGCTAATT TTTGTAATTT TAGTAGAGAC     1316

AGGGTTTCAC CATGTTGCCC AGGCTGGTTT CGAACTCCTG ACCTCAGGTG ATCCACCCGC     1376

CTCGGCCTCC CAAAGTGCTG GGATTACAGG CTTGAGCCCC CGCGCCCAGC CATCAAAATG     1436

CTTTTTATTT CTGCATATGT TTGAATACTT TTTACAATTT AAAAAAATGA TCTGTTTTGA     1496

AGGCAAAATT GCAAATCTTG AAATTAAGAA GGCAAAATGT AAAGGAGTCA ACTATAAAT     1556

CAAGTATTTG GGAAGTGAAG ACTGGAAGCT AATTTGCATA AATTCACAAA CTTTTATACT     1616

CTTTCTGTAT ATACATTTTT TTTCTTTAAA AACAACTAT GGATCAGAAT AGCCACATTT      1676

AGAACACTTT TTGTTATCAG TCAATATTTT TAGATAGTTA GAACCTGGTC CTAAGCCTAA     1736

AAGTGGGCTT GATTCTGCAG TAAATCTTTT ACAACTGCCT CGACACACAT AAACCTTTTT     1796

AAAAATAGAC ACTCC                                                      1811
```

(2) INFORMATION FOR SEQ ID NO:2:

(i) SEQUENCE CHARACTERISTICS:
  (A) LENGTH: 80 amino acids
  (B) TYPE: amino acid
  (D) TOPOLOGY: linear (ii) MOLECULE TYPE: protein (xi) SEQUENCE DESCRIPTION: SEQ ID NO:2:

```
Met  Gly  Arg  Ala  Met  Val  Ala  Arg  Leu  Gly  Leu  Gly  Leu  Leu  Leu  Leu
-26  -25                 -20                      -15

Ala  Leu  Leu  Leu  Pro  Thr  Gln  Ile  Tyr  Ser  Ser  Glu  Thr  Thr  Thr  Gly
-10                  -5                            1                       5

Thr  Ser  Ser  Asn  Ser  Ser  Gln  Ser  Thr  Ser  Asn  Ser  Gly  Leu  Ala  Pro
                 10                      15                       20

Asn  Pro  Thr  Asn  Ala  Thr  Thr  Lys  Ala  Ala  Gly  Gly  Ala  Leu  Gln  Ser
           25                      30                       35

Thr  Ala  Ser  Leu  Phe  Val  Val  Ser  Leu  Ser  Leu  Leu  His  Leu  Tyr  Ser
           40                      45                       50
```

(2) INFORMATION FOR SEQ ID NO:3:

(i) SEQUENCE CHARACTERISTICS:
  (A) LENGTH: 1800 base pairs
  (B) TYPE: nucleic acid
  (C) STRANDEDNESS: single
  (D) TOPOLOGY: linear (ii) MOLECULE TYPE: DNA (genomic)

(vi) ORIGINAL SOURCE:
  (A) ORGANISM: Mus musculus (vii) IMMEDIATE SOURCE:
  (A) LIBRARY: Mouse
  (B) CLONE: M1/69-J11d Heat-Stable Antigen (ix) FEATURE:
  (A) NAME/KEY: sig_peptide (B) LOCATION: 73..150

(ix) FEATURE:
 (A) NAME/KEY: mat_peptide
 (B) LOCATION: 151..300

(ix) FEATURE:
 (A) NAME/KEY: CDS
 (B) LOCATION: 73..303

(xi) SEQUENCE DESCRIPTION: SEQ ID NO:3:

| | | | | |
|---|---|---|---|---|
| CCCCGCGCGA | GCTTAGCAGA | TCTCCACTTA | CCGAACATCT | AGAGAGTCGC GCCGCGCGCC | 60 |

| | | | | | | | | | | | |
|---|---|---|---|---|---|---|---|---|---|---|---|
| GACGGAGCGG | AC ATG | GGC | AGA | GCG | ATG | GTG | GCC | AGG | CTA | GGG CTG GGG | 108 |
| | Met | Gly | Arg | Ala | Met | Val | Ala | Arg | Leu | Gly Leu Gly | |
| | -26 | -25 | | | -20 | | | | | -15 | |

| | | | | | | | | | | | | |
|---|---|---|---|---|---|---|---|---|---|---|---|---|
| TTG | CTG | CTT | CTG | GCA | CTG | CTC | CTA | CCC | ACG | CAG | ATT TAC TGC AAC CAA | 156 |
| Leu | Leu | Leu | Leu | Ala | Leu | Leu | Leu | Pro | Thr | Gln | Ile Tyr Cys Asn Gln | |
| | | | -10 | | | | | -5 | | | 1 | |

| | | | | | | | | | | | | |
|---|---|---|---|---|---|---|---|---|---|---|---|---|
| ACA | TCT | GTT | GCA | CCG | TTT | CCC | GGT | AAC | CAG | AAT | ATT TCT GCT TCC CCA | 204 |
| Thr | Ser | Val | Ala | Pro | Phe | Pro | Gly | Asn | Gln | Asn | Ile Ser Ala Ser Pro | |
| | 5 | | | | | | 10 | | | | 15 | |

| | | | | | | | | | | | | |
|---|---|---|---|---|---|---|---|---|---|---|---|---|
| AAT | CCA | AGT | AAC | GCT | ACC | ACC | AGA | GGG | GGT | GGC | AGC TCC CTG CAG TCC | 252 |
| Asn | Pro | Ser | Asn | Ala | Thr | Thr | Arg | Gly | Gly | Gly | Ser Ser Leu Gln Ser | |
| | 20 | | | | 25 | | | | | 30 | | |

| | | | | | | | | | | | | |
|---|---|---|---|---|---|---|---|---|---|---|---|---|
| ACA | GCT | GGT | CTC | CTG | GCT | CTC | TCT | CTC | TCT | CTT | CTA CAT CTC TAC TGT | 300 |
| Thr | Ala | Gly | Leu | Leu | Ala | Leu | Ser | Leu | Ser | Leu | Leu His Leu Tyr Cys | |
| 35 | | | | 40 | | | | | 45 | | 50 | |

| | | | | | |
|---|---|---|---|---|---|
| TAGAGACTCA | GGCCAGGAAA | CGTCTCTACT | TCCCCATCTT | CTACACCTAC | CCCAAATGGC | 360 |
| AACCACAAGT | CCAATGTGAT | CAGGAAGAAA | CAGGTCCACC | TCGAATTGGC | TGTTACCATA | 420 |
| TCTCAACAGA | AAACACGGAG | AATTCGAAAT | TCGACGGGAT | TAAAGGACGC | GTGAAAGGTT | 480 |
| TGAGAGAAGA | GAGATGCCGC | TATTGAATCT | GCTGGAGTTT | ACATCCCAA | GATGAAGACA | 540 |
| GCATTCAGAA | TTGATGTGAT | TTCCTTGAAT | CGTGGCTTAG | GAAATGTGGA | CACTTAAAAC | 600 |
| TCTCACTTGA | AATTGGGCAC | AGGTTTGATG | TAGAGATAAG | GACGGGGTGC | GGAATGGAGA | 660 |
| CCCATTTTGT | CATTGATTCA | TCTGACCGAT | AAGGCCATAG | TGCAGTTAGG | TGATATTCGA | 720 |
| AAGCTTCTTT | GATGCTCTTT | ATGTATATGT | TGGAAGGAAC | TACCAGGCGT | TGCTTTAAAT | 780 |
| TCCCAATGTG | TTGTTTCGTT | ACTACTAATT | TAATACCGTA | AGCTCTAGGT | AAAGTTCCAT | 840 |
| GTTGTTGAAC | TCTGACTGTT | CTCTTTGGAA | TTGAACCTTT | TGCATCCTCC | TCCTGTGGCT | 900 |
| TTAGGTCTGA | CATTGTATTT | GACCTTTACT | AGTAATTAAC | ATGTGCCAGG | CAATGGTGGA | 960 |
| TTGGAACCCA | TCCCCAAGTC | CAGCCACCAC | TGAATAAATC | TGATTTCAAA | AGTCAAACAG | 1020 |
| TAGACATTTC | CCATTGTCGT | TTCTCACTCA | CCACAAGCAC | CAAATTCACT | AGAGTACACT | 1080 |
| GGTTCCAGAG | AGCAGAATCA | TGTTGGCCTT | GGCTAATTTC | AAAATGCTGT | CTTTTACTTT | 1140 |
| GGTATATGTT | GAGGGCTTTT | CATAATTTAA | AGTGTGTTCT | GTTAGCAAGG | CAAAAATTAT | 1200 |
| GAGTCTTAAT | TCTACAGGCA | AATATGCAAA | GGAGCCAAAA | CTGTAAACCC | AGCATTTGGG | 1260 |
| ATGTGAAGAC | TGGAAGCTAA | CTCTCATTGA | ATTCACAAAG | TCTTTTATAC | AATTTCTGTA | 1320 |
| CATACTTTTT | TTTTTTTTAA | GAGAAAAACA | AACGGTGGAT | CAGAATAGCC | ACGTTTGGAA | 1380 |
| TACTTTGGTT | ATCCATTCAT | ATTTTTAGAT | AGTTATTGGT | CCTGTGCCTG | AAAGGGGGCT | 1440 |
| TGGTTCTACC | GTAAGTTTTT | CCAATTTCCT | TGATATACAC | ATACCTTCTA | AAACCTAGAC | 1500 |
| ATTTCCTGAA | AAAAATCTTT | TGTTCGCATG | GTCACACACT | GATGCTTACC | CGTACAGTAG | 1560 |
| TCTTGATAAC | CAGAGTCATT | TTCTCCATCT | TTAGAAACCT | TCCTGGAAGA | AGGAGAGCTC | 1620 |
| ACAGACCCGA | AGCTACTGTG | TGTGTGAATG | AACACTCCCC | TTGCCTCACA | CCTGAATGCT | 1680 |

-continued

```
GTACATCTAT   TTGATTGTAA   ATTGTGTTTG   TGTATTTATG   CTTTGATTCA   TAGTAACTTC        1740

TCATGTTATG   GAATTGATTT   GCATTGAACA   CAAACTGTAA   ATAAAAGAAA   GAAATGGCGG        1800
```

( 2 ) INFORMATION FOR SEQ ID NO:4:

( i ) SEQUENCE CHARACTERISTICS:
        ( A ) LENGTH: 76 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Gly  Arg  Ala  Met  Val  Ala  Arg  Leu  Gly  Leu  Gly  Leu  Leu  Leu  Leu
-26  -25                      -20                      -15

Ala  Leu  Leu  Leu  Pro  Thr  Gln  Ile  Tyr  Cys  Asn  Gln  Thr  Ser  Val  Ala
-10                      -5                       1                       5

Pro  Phe  Pro  Gly  Asn  Gln  Asn  Ile  Ser  Ala  Ser  Pro  Asn  Pro  Ser  Asn
               10                      15                      20

Ala  Thr  Thr  Arg  Gly  Gly  Gly  Ser  Ser  Leu  Gln  Ser  Thr  Ala  Gly  Leu
          25                      30                      35

Leu  Ala  Leu  Ser  Leu  Ser  Leu  Leu  His  Leu  Tyr  Cys
     40                      45                      50
```

METHOD OF USING CD24 AS A CELL MARKER

This application is a continuation of U.S. application Ser. No. 08/538,052 filed Oct. 2, 1995, now abandoned, which is a continuation of U.S. Ser. No. 08/151,672 filed Nov. 15, 1993, now abandoned.

FIELD OF THE INVENTION

The invention relates generally to a selectable cell marker and to a method of using the selectable marker to identify a cell. The invention also relates to a method of identifying a recombinant cell expressing an exogenous gene by means of a selectable marker.

BACKGROUND OF THE INVENTION

Viruses such as recombinant retroviruses have been used as a vehicle for gene transfer based on their potential for highly efficient infection and non-toxic integration of their genome into a wide range of cell types. The transfer of exogenous genes into mammalian cells may be used, for example in gene therapy to correct an inherited or acquired disorder through the synthesis of missing or defective gene products in vivo. The expression of exogenous genes in cells may be useful in somatic gene therapy, to correct hereditable disorders at the level of the gene. Hemopoietic stem cells are particularly suited to somatic gene therapy as regenerative bone marrow cells may be readily isolated, modified by gene transfer and transplanted into an immunocompromised host to reconstitute the host's hemopoietic system.

Evidence points to a hierarchy of stem cells with differing potentials for sustaining hematopoiesis when transplanted in vivo. Cells with long term hematopoietic reconstituting ability can be distinguished by a number of physical and biological properties from cells that only generate mature progeny in short-term in vivo or in vitro clonogenic assays (Hodgson, G. S. & Bradley, T. R., Nature, Vol. 281, pp. 381–382; Visser et al., J. Exp. Med., Vol. 59, pp. 1576–1590, 1984; Spangrude et al., Science, Vol. 241, pp. 58–62, 1988; Szilvassy et al., Blood, Vol. 74, pp. 930–939, 1989; Ploemacher, R. E. & Brons, R. H. C., Exp. Hematol., Vol. 17, pp. 263–266, 1989).

Gene therapy involving hone marrow transplant with recombinant primary hemopoietic stem cells requires efficient gene transfer into the stem cells. As a very small number of primary stem cells can reconstitute the entire host hemopoietic system it is important that the transferred gene be efficiently expressed in the recombinant stem cells transferred. While potentials for transfer efficiency approach 100%, such levels may not be realized due to low viral titre and the requirement that target cells be actively replicating at the time of infection (Miller et al., MC Biol., 10:4239, 1990 and Springetti et al., J. Virology 63:3865, 1989). Moreover, expression of the transferred gene may not be at desired levels necessitating extensive analysis to identify critical regulatory sequences.

In an effort to identify and enrich for successfully infected target cells expressing high levels of the transferred gene workers have included dominant selectable markers in their retroviral vectors. The most widely used markers have been cDNAs encoding proteins which confer resistance to toxic or inhibitory compounds such as neomycin (Dick et al., Cell. 42:71, 1985; Magli et al., Proc. Natl. Acad. Sci. USA 84:789, 1987; Eglitis et al., Science 230:1395, 1985; Keller et al., Nature 318:149, 1985; Kwok et al., Proc. Natl. Acad. Sci. USA 83:4552, 1986; Eglitis et al., Blood 71:717, 1988; Hock et al., Nature 320:275, 1986; Hogge et al, Blood 69:611, 1987; Anklesaria et al., Exp. Hematol. 15:195, 1987; Keller et al., CSHSQB LI:1027, 1986; Bernstein et al., CSHSQB LI:1083, 1986; Uchidu at al., J. Immunol. 136:1876, 1986; Kohn et al., Blood Cells 13:285, 1987; Chang et al., MC Biol. 7:854, 1987; Karlsson et al., Proc. Natl. Acad. Sci. USA 84:2411, 1987; Yang et al. MC Biol. 7:3923, 1987; Laneuville et al., Blood 71:811, 1988; Karlsson et al., Proc. Natl. Acad. Sci. USA 85:6062, 1988; Valerio et al. Gene 84:419, 1989; Hock et al., Blood 74:876, 1989; Kung et al., Proc. Natl. Acad. Sci. USA 87:9803, 1990; Dumenil et al., MC Biol. 9:4541, 1989; Rixon et al., Biochemistry 29:4393, 1990; Hesdorffer at al., DNA and Cell Biol. 9:717, 1990; Kasid et al., Proc. Natl. Acad. Sci. USA 87:473, 1990; Fink et al., Proc. Natl. Acad. Sci. USA 87:2334, 1990; Green et al., Proc. Natl. Acad. Sci. USA 88:8475, 1991; Morecki et al., Cancer Immunol. Immunother. 32:342, 1991; Culver et al., Proc. Natl. Acad. Sci. USA 88:3155, 1991; Dick et al., Blood 78:624, 1991; Shimada et al., J. Clinical Investigation 88:1043, 1991; Beck-Engeser et al., Human Gene Therapy 2:61, 1991; Apperley et al., Seminars In Hematol. 28:170, 1991; Fauser, J. Cell. Biochem. 45:353, 1991; Hawley et al., Leukemia Research 15:659, 1991; Laneuville et al., Blood 80:1788, 1992; Martiart et al., Blood 81:502, 1993), hygromycin (Yang et al., MC Biol. 7:3923, 1987; Miller et al., CSHSQB 51:1013, 1986; Palmer, TD, Proc. Natl. Acad. Sci. USA, 84:1055, 1987), chloramphenicol (Wood et al., CSHSQB 51:1027, 1986), methotrexate (Miller, AD, MC Biol., 5:431, 1985; Corey et al., Blood 75:337, 1990; Williams et al., Proc. Natl. Acad. Sci. USA, 83:2566, 1986; Stead et al., Blood 71:742, 1988), mycophenolic acid (Stuhlmann et al., Proc. Natl. Acad. Sci. USA 81:7151, 1984), or various chemotherapeutic agents (Guild et al., Proc. Natl. Acad. Sci USA 85:1595, 1988; Kane et al., Gene 84:439, 1989; Choi et al., Proc. Natl. Acad. Sci. USA; Sorrentino, et al., Science 257:99, 1992). However, use of these markers in selection protocols carry disadvantages such as non-specific toxicity associated with exposure of the cells to the inhibitory drug or compound as well as difficulties in quantitating expression levels. As an alternative, markers such as the bacterial β-galactosidase gene (lacZ) and the human placental alkaline phosphatase gene have been employed both as a selectable marker in vitro (Strair, R. K. et al., Nucleic Acids Res. 18:4759, 1990; Strair et al., Nucleic Acids Research 18:4759, 1988; Nolan et al., Prod. Natl. Acad. Sci. USA 85:2603, 1988) and as a reporter molecule in vitro (Strair at al., Blood 76:1201, 1990; Wilson et al., Prod. Natl. Acad. Sci. 85:3014, 1988; Fields-Berry et al., Prod. Natl. Acad. Sci. USA 89:693, 1992) and in vivo (Nabel at al., Science 249:1285, 1990; Nabel et al., Science 244:1342, 1989; Ferry et al., Prod. Natl. Acad. Sci. USA 88:8377, 1991; Price et al., Prod. Natl. Acad. Sci. USA 94:156, 1987). The presence of an endogenous mammalian lysosomal β-galactosidase as well as problems in achieving high levels of expression of the exogenous β-gal gene have confounded its widespread utilization as a dominant marker.

Several studies have documented the feasibility of retroviral mediated transfer of genes encoding cell surface molecules including CD8 (Hollander et al., J. Immunology 149:438, 1992), the alpha and beta chains of the T cell receptor (Green et al., Proc. Natl. Acad. Sci. USA 88:8475, 1991; Kang et al., Proc. Natl. Acad. Sci. USA 87:9803, 1990), and several major histocompatibility antigens (Shafer et al., Proc. Natl. Acad. Sci. USA 88:9760, 1991; Korman et al., Proc. Natl. Acad. Sci. USA 84:2150, 1987; Yang et al., MC Biol. 7:3923, 1987; Emery et al., Transplantation Proceedings 24:468, 1992; Sykes et al., Transplantation 55:197, 1993). The possibility of using such genes to select for and quantitate gene expression in virally transduced target cells using fluorescence activated cell sorting (FACS) has also been suggested. Strair et. al., J. Virology 62:4756, 1988, for example, utilized vectors containing either the human transferrin receptor or the human lymphocyte antigen, Leu-1, in combination with FACS to detect and quantitate gene transfer and expression in NIH-3T3 and primary baby rat kidney cells, as well as the ability to select for cells with varying levels of expression of the transferred gene. More recently, both the IL-2 receptor gene (Olsen et al., Nucleic Acids Research 21:663, 1993) and the multi-drug resistance gene (Choi et al., Proc. Natl. Acad. Sci. 88:7386, 1991), coding for an efficient efflux pump, have been used both as a means of analyzing and quantitating gene expression in virally transduced cells, or as a means of selecting them using FACS.

The transfer of foreign genes into a reconstituted host hemopoietic system has been limited by the availability of a selectable marker which permits the rapid and non-toxic selection of cells which are efficiently expressing the transferred gene. Currently available selection markers may not be suitable for primary hemopoietic stem cells since they may alter the proliferative ability or biological characteristics of the cells. The transfer of foreign genes into a reconstituted host hemopoietic system has also been limited by the availability of a viral vector capable of expression in hemopoietic stem cells, especially where more than one transcriptional unit is present in the vector (Botrell, D. R. L. et al., 1987, Mol. Biol. Med. 4:229).

CD24 is a signal transducing molecule found on the surface of most human B cells that can modulate their responses to activation signals (Ling, Pezutto). The cD24 CDNA (approximately 300 bps) has been cloned (Kay, R. et al, 1991, J. Immunol. 147:1412) and encodes a mature peptide of only 31 to 35 amino acids that is extensively glycosylated and attached to the outer surface of the plasma membrane by a glycosyl phosphatidylinositol lipid anchor. M1/69-J11d heat stable antigen is a genetically similar homologous murine peptide widely expressed on a variety of hemopoietic cell types (Kay, R. et al., 1990, J. Immunol. 145:1952).

SUMMARY OF THE INVENTION

The present inventor has used the cell surface protein CD24 as a dominant marker in a recombinant viral vector. A nucleotide sequence encoding the cell surface protein CD24 in a recombinant viral vector was used to infect hematopoietic stem cells. Cells infected with the recombinant viral vector were rapidly and non-toxically selected for in vitro using fluorescence activated cell sorting (FACS). A good correlation between proviral copy number and expression of selectable marker was demonstrated.

The inventor also used the recombinant viral vector to successfully transfer and express the CD24 gene in primitive hemopoietic stem cells which were able to repopulate lethally irradiated recipients. Foreign CD24 antigen expression in repopulated animals persisted for up to a minimum of 4 months post transplantation suggesting that the biological function of the repopulated hemopoietic cells was not affected by the expression of the CD24 antigen. All the hemopoietic lineages were found to express the transferred CD24, including granulocytes, macrophages, pro-erythrocytes, erythrocytes and T and B lymphocytes. Therefore, the cell surface protein CD24 is particularly useful as a marker for hematopoietic stem cells capable of long term repopulation in vivo and facilitates its use as a selectable marker in gene therapy.

The recombinant viral vectors also have the advantage that the nucleotide sequence encoding the marker is very small. In particular, the use of CD24 as a dominant marker in recombinant viral vectors is attractive as it leaves a large amount of space for the insertion of additional genes of interest such as those coding for exogenous genes.

The present invention therefore provides a method of marking a cell comprising introducing into the cell a nucleotide sequence encoding a cell surface protein and having substantial homology to the nucleotide sequence encoding CD24, and expressing the cell surface protein on the cell.

In a preferred embodiment of the invention a recombinant viral vector is used to introduce the nucleotide sequence into the cell. Therefore, the invention contemplates a recombinant viral vector having a nucleotide sequence encoding a cell surface protein and having substantial homology to the nucleotide sequence encoding CD24. Preferably, the nucleotide sequence is operatively linked to one or more regulatory elements. In one embodiment, the nucleotide sequence with substantial homology to the nucleotide sequence encoding CD24 is the nucleotide sequence as shown in FIG. 8 and in the Sequence Listing as SEQ. ID. NO. 1. In a second embodiment, the nucleotide sequence is the nucleotide sequence coding for the murine M1/69-J11d heat stable antigen as shown in FIG. 9 and in the Sequence Listing as SEQ.ID.NO. 2.

The recombinant viral vector of the invention may be used as a marker for an exogenous gene to be expressed in a host cell. Thus, the recombinant vector of the invention may also comprise a nucleotide sequence coding for an exogenous gene operatively linked to one or more expression control sequences. The exogenous gene may be a gene encoding a protein which confers resistance to toxic or inhibitory compounds. The exogenous gene may also encode a biologically active protein.

In a preferred embodiment of the invention the recombinant viral vector is JZenCD24tkneo.

A recombinant cell including a recombinant viral vector of the invention is also provided. The recombinant cell may be a viral producer cell which is used to infect a cell, and the cell so infected. In an embodiment of the invention the cell to be infected is from a first animal species and the recombinant viral vector has a nucleotide sequence with substantial homology to the nucleotide sequence encoding CD24 of a different animal species. For example, if the cell is from a human, the recombinant viral vector has a nucleotide sequence encoding murine M1/69-J11d heat stable antigen. If the cell is a murine cell, the recombinant viral vector has a nucleotide sequence encoding human CD24.

The invention further provides a method of identifying a cell and progeny thereof comprising: providing a cell; infecting the cell with a recombinant viral vector of the invention under suitable conditions to allow expression of the cell surface protein on the cell; and, identifying the cell and progeny thereof by detecting expression of the cell surface protein on the cell or progeny thereof.

In an embodiment of the invention the recombinant viral vector has an exogenous gene and expression control sequences operatively linked thereto and the method is used to monitor exogenous gene expression. In particular, a method is provided for monitoring exogenous gene expression in a cell and in progeny thereof comprising: providing a cell; infecting the cell with a recombinant viral vector having an exogenous gene and one or more expression control sequences operatively linked thereto, and a nucleotide sequence encoding a cell surface protein and having substantial homology to the nucleotide sequence encoding CD24 and one or more regulatory elements operatively linked thereto, under suitable conditions to allow expression in the cell of the exogenous gene and the cell surface protein and; identifying the cell and progeny thereof expressing the exogenous gene by detecting cells expressing the cell surface protein. In a preferred embodiment the cell is a hemopoietic cell.

Cells infected with a recombinant viral vector of the invention and expressing the cell surface protein may be transplanted into a host, and the cell and progeny thereof may be identified after transplantation by removing biological samples from the host, and assaying for cells expressing the cell surface protein. A recombinant viral vector of the invention may be directly introduced in into a host.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will be better understood with reference to the drawings in which:

FIG. 8 shows the nucleotide sequence encoding CD24 (SEQ ID NO:1); and

DETAILED DESCRIPTION OF THE INVENTION

Figure 1:
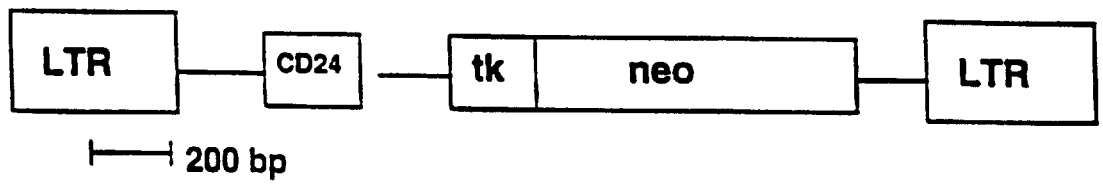
FIG. 1 is a cartoon of the JZenCD24tkneo retroviral vector.

As hereinbefore mentioned, the present invention provides a method of marking a cell comprising introducing a nucleotide sequence encoding a cell surface protein and having substantial homology to the nucleotide sequence encoding CD24, and expressing the cell surface protein on the cell.

The nucleotide sequence may be introduced into the cell by a variety of methods known in the art for the introduction of nucleotide sequences into cells. Physical methods of introducing DNA into a cell include microinjection (Anderson, W. F. et al., 1980, Proc. Natl. Acad. Sci. USA 77:5299) and electroporation (Neumann, E. et al., 1982, EMBO J., 1:841). Chemical methods of introducing exogenous DNA into cells include coprecipitation with calcium phosphate and incorporation of DNA into liposomes (Felgner, P. L. et al., 1987, Proc. Natl. Acad. Sci. USA 84:7413), DEAE-dextran (Sussman, D. J. and Milman, G., 1984, Mol. Cell Biol. 4:1641). Bacterial or viral vectors may also be used to introduce the exogenous DNA into the cell. Methods and vectors for infecting cells with exogenous DNA are described, for example, in Old, R. W. and Primrose, S. B. Principles of Gene Manipulation, Blackwell Scientific Publications, Oxford.

In a preferred embodiment of the invention, the nucleotide sequence is introduced using a recombinant viral vector. The recombinant viral vector has a nucleotide sequence encoding a cell surface protein having substantial homology to the nucleotide sequence encoding CD24.

The recombinant viral vector may be constructed using a variety of viruses which been adapted as vectors, including adenoviruses (Morin, J. A. et al, 1987, Proc. Natl. Acad. Sci. USA 84:4626) retroviruses (Varmus, H., 1988, Science 244:1275) and DNA viruses (Palella, T. D. et al., 1989, Gene 80:137), and herpes viruses such as Herpes simplex virus. Preferably, the recombinant viral vector is constructed using a retrovirus. Retroviruses may be selected for a wide range of host target cells, including avian, mammalian and other animal cells. Moloney murine leukemia virus and LNLG (Bender, M. A. et al., 1987, J. Virol. 61:1639) are examples of suitable retroviruses. In a particularly preferred embodiment of the invention, the retroviral vector is constructed from the Jzen1 backbone, derived from the myeloproliferative sarcoma virus (Johnson et al., 1989, EMBO J. 8:441).

Viral vectors may be constructed from cloned retroviral DNA using conventional techniques. A viral vector may be constructed by deleting the structural genes required for viral replication from the viral genome, such as the gag gene which encodes for group specific antigens, the pol gene which encodes for reverse transcriptase and invertase and the env gene which encodes the envelope protein (Cepko, C. L. et al., (1984, Cell, 37:1053). A gene(s) of interest, for example the gene encoding the marker and optionally an exogenous gene, may then be ligated into the deleted genome of the virus.

The recombinant viral vector of the invention encodes a cell surface protein and has a nucleotide sequence with substantial homology to the nucleotide sequence encoding CD24. The nucleotide sequences may comprise all, substantially all, or a portion of the nucleotide sequence encoding CD24 as shown in FIG. 8 or in the Sequence Listing as SEQ ID NO. 1, so long as the cell surface protein of CD24, or an epitope thereof is expressed on a cell infected with a recombinant viral vector having the nucleotide sequence.

CD24 molecules have been identified as a set of glycoproteins with apparent molecular masses ranging from 35 to 45 kDa (Pirrucello, S. J. and LeBien, T. W., 1986, J. Immunol. 136:3779). CD24 is distinguished from other signal transducing proteins by its very short peptide and complete lack of physical connection with the interior of the cell. The minimalist structure of CD24 leaves it incapable of most biological activities described for other cell surface transducers, such as ion channel formation, enzymatic activities or direct interaction with cytosolic signal transducing proteins.

Figure 9B:
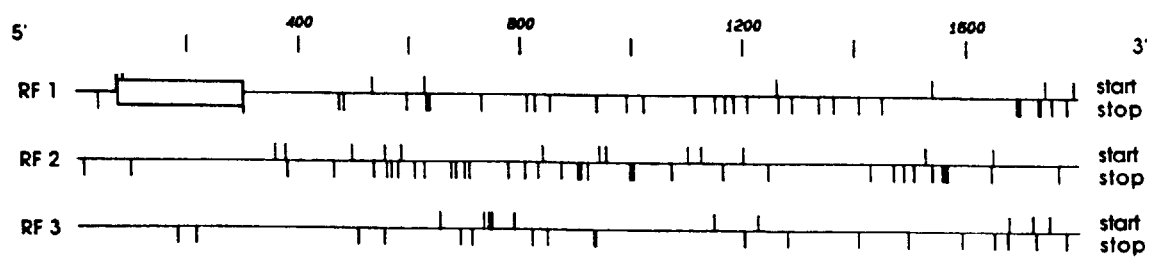
FIG. 9 shows the nucleotide sequence coding for the murine M1/69-J11d heat stable antigen (SEQ ID NO:4).

Nucleotide sequences having substantial homology to the nucleotide sequence encoding CD24 include the nucleotide sequence encoding M1/69-J11d. The coding region of M1/69-J11d is shown in Kay, R. et al, 1990 (J. Immunol. 145:1952) and is shown in FIG. 9 or in the Sequence Listing as SEQ ID. NO. 2. Although various heterogeneous forms of the M1/69-J11d antigen are known, they appear to be the product of a single gene and the heterogeneity may arise from cell type-specific processing of the product of the gene. Thus, nucleotide sequences having substantial homology to the CD24 coding region may be obtained from a family of homologous genes, as the structure of the CD24 peptide and antigen have been strongly conserved in mammalian evolution (Kay, R. et al, 1990 J. Immunol. 145:1952).

Nucleotide sequences having substantial homology to the nucleotide sequence encoding CD24 may use, for example, be identified by screening with CD24 cDNA or probes of highly conserved regions thereof. The nucleotide sequence encoding CD24 itself was cloned based on its homology to a cDNA of the related murine M1/69-J11d heat stable antigen (Kay at al., 1991, J. Immunol. 147:1412). One could also use the polymerase chain reaction (PCR) and oligonucleotide primers which amplify nucleotide sequences having substantial homology to the nucleotide sequence encoding CD24 (Mullis el al., U.S. Pat. No. 4,863,195 and Mullis, U.S. Pat. No. 4,683,202 and M. A. Innis and D. H. Gelfand, PCR Protocols, A Guide to Methods and Applications M. A. Innis, D. H. Gelfand, J. J. Sninsky and T. J. White eds, pp3–12, Academic Press 1989). Nucleotide sequences having substantial homology to the nucleotide sequence encoding CD24 may also be constructed by chemical synthesis and enzymatic ligation reactions using procedures known in the art.

The nucleotide sequence with substantial homology to the nucleotide sequence encoding CD24 is preferably operatively linked to one or more regulatory elements. Suitable regulatory elements may be derived from a variety of sources, including bacterial, fungal, viral, mammalian, or insect genes. Selection of appropriate regulatory elements is dependent on the host cell to be infected with the recombinant viral vector, and may be readily accomplished by one of ordinary skill in the art. Examples of regulatory elements include: a transcriptional promoter and enhancer or RNA polymerase binding sequence, a ribosomal binding sequence, including a translation initiation signal. Additionally, depending on the host cell chosen other genetic elements, such as an origin of replication, additional DNA restriction sites, enhancers, and sequences conferring inducibility of transcription may be incorporated into the vector. The regulatory elements are preferably the regulatory sequences of the virus used to construct the recombinant viral vector. For example, if a retrovirus is used the regulatory elements may be the long terminal repeat sequences of the virus.

The recombinant viral vector may also contain a nucleotide sequence encoding for an exogenous gene. By exogenous gene is meant any gene which does not originate from the vector, and/or a cell to be infected, and which may be ligated into the vector. The exogenous gene may encode a protein which confers resistance to toxic or inhibitory compounds. Examples of such exogenous genes are the genes encoding neomycin (Dick et al., Cell. 42:71, 1985; Magli et al., Proc. Natl. Acad. Sci. USA 84:789, 1987; Eglitis at al., Science 230:1395, 1985; Keller at al., Nature 318:149, 1985; Kwok et al., Proc. Natl. Acad. Sci. USA 83:4552, 1986; Eglitis et al., Blood 71:717, 1988; Hock et al., Nature 320:275, 1986; Hogge et al, Blood 69:611, 1987; Anklesaria et al., Exp. Hematol. 15:195, 1987; Keller et al., CSHSQB LI:1027, 1986; Bernstein et al., CSHSQB LI:1083, 1986; Uchidu et al., J. Immunol. 136:1876, 1986; Kohn et al., Blood Cells 13:285, 1987; Chang et al., MC Biol. 7:854, 1987; Karlsson et al., Proc. Natl. Acad. Sci. USA 84:2411, 1987; Yang at al. MC Biol. 7:3923, 1987; Laneuville et al., Blood 71:811, 1988; Karlsson et al., Proc. Natl. Acad. Sci. USA 85:6062, 1988; Valerio et al. Gene 84:419, 1989; Hock et al., Blood 74:876, 1989; Kung et al., Proc. Natl. Acad. Sci. USA 87:9803, 1990; Dumenil et al., MC Biol. 9:4541, 1989; Rixon et al., Biochemistry 29:4393, 1990; Hesdorffer et al., DNA and Cell Biol. 9:717, 1990; Kasid et al., Proc. Natl. Acad. Sci. USA 87:473, 1990; Fink et al., Proc. Natl. Acad. Sci. USA 87:2334, 1990; Green et al., Proc. Natl. Acad. Sci. USA 88:8475, 1991; Morecki et al., Cancer Immunol. Immunother. 32:342, 1991; Culver et al., Proc. Natl. Acad. Sci. USA 88:3155, 1991; Dick et al., Blood 78:624, 1991; Shimada et al., J. Clinical Investigation 88:1043, 1991; Beck-Engeser et al., Human Gene Therapy 2:61, 1991; Apperley et al., Seminars in Hematol. 28:170, 1991; Fauser, J. Cell. Biochem. 45:353, 1991; Hawley et al., Leukemia Research 15:659, 1991; Laneuville et al., Blood 80:1788, 1992; Martiart at al., Blood 81:502, 1993), hygromycin (Yang et al., MC Biol. 7:3923, 1987; Miller et al., CSHSQB 51:1013, 1986; Palmer, TD, Proc. Natl. Acad. Sci. USA, 84:1055, 1987), chloramphenicol (Wood et al., CSHSQB 51:1027, 1986), methotrexate (Miller, AD, MC Biol., 5:431, 1985; Corey et al., Blood 75:337, 1990; Williams at al., Proc. Natl. Acad. Sci. USA, 83:2566, 1986; Stead et al., Blood 71:742, 1988), mycophenolic acid (Stuhlmann et al., Proc. Natl. Acad. Sci. USA 81:7151, 1984), or various chemotherapeutic agents (Guild et al., Proc. Natl. Acad. Sci USA 85:1595, 1988; Kane et al., Gene 84:439, 1989; Choi et al., Proc. Natl. Acad. Sci. USA; Sorrentino, et al., Science 257:99, 1992). The bacterial β-galactosidase gene (lacZ) and the human placental alkaline phosphatase gene may also be used in the recombinant viral vector of the invention (Strair, R. K. et al., Nucleic Acids Res. 18:4759, 1990; Strair et al., Nucleic Acids Research 18:4759, 1988; Nolan at al., Prod. Natl. Acad. Sci. USA 85:2603, 1988; Strair et al., Blood 76:1201, 1990; Wilson et al., Prod. Natl. Acad. Sci. 85:3014, 1988; Fields-Berry et al., Prod. Natl. Acad. Sci. USA 89:693, 1992; Nabel et al., Science 249:1285, 1990; Nabel et al., Science 244:1342, 1989; Perry et al., Prod. Natl. Acad. Sci. USA 88:8377, 1991; Price et al., Prod. Natl. Acad. Sci. USA 84:156, 1987).

The exogenous gene may also encode a biologically active protein. A biologically active protein may be selected to modify the genotype and phenotype of the cell. For example, the exogenous gene may be selected for gene augmentation to modify the expression of mutant genes in the cell, or to restore genetic function by introducing the exogenous gene into non-specific sites in the cell's genome.

The exogenous gene may be operatively linked to one or more expression control sequences. The exogenous genes may be under the same regulatory control as the nucleotide sequence having substantial homology to the nucleotide sequence encoding CD24. For example, the expression control sequences may be the long terminal repeat sequences of the virus used to construct the vector. The exogenous gene is preferably under different regulatory control than the nucleotide sequences. Expression control sequences include the regulatory elements described above. In a preferred embodiment, the exogenous gene may be under the regulatory control of an enhancer such as a polyoma virus enhancer tandem repeat and a promoter such as a thymidine kinase gene promoter.

In a particularly preferred embodiment of the invention the recombinant viral vector is JZenCD24tkneo as shown in FIG. 1. The retroviral vector Jzentkneo may be constructed by inserting a neomycin resistance gene under the regulatory control of a polyoma virus enhancer tandem repeat and a thymidine kinase gene promoter into the Jzen1 vector. The coding region of the CD24 gene is then inserted into the Xho 1 site to produce the novel vector JZenCD24tkneo.

A recombinant cell including a recombinant viral vector of the invention is also contemplated by the present invention. The recombinant viral vector may be introduced into a wide variety of prokaryotic and eukaryotic host cells, including bacterial, mammalian, yeast or other fungi, viral, plant, or insect cells. Methods for transforming or transfecting such cells to express foreign DNA are well known in the art (see, e.g., Itakura et al., U.S. Pat. No. 4,704,362; Hinnen et al., PNAS USA 75:1929–1933, 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al. Molecular Cloning A Laboratory Manual, 2nd edition, Cold Spring Harbor Laboratory Press, 1989, all of which are incorporated herein by reference).

The recombinant cell may be a viral producer cell which is used to infect a selected cell. A viral producer cell may be prepared by introducing a recombinant viral vector of the invention which has the viral genes required for viral replication deleted from the viral genome as described above, into a packaging cell line in which the structural genes required for viral replication, devoid of packaging signals, have previously been transfected (Nabel, E. G., 1991, IACC 17:1898). The structural genes required for viral replication provided in the packaging cell line allow production of a virus particle containing the defective nucleotide sequences of the recombinant viral vector, and the virus is capable of infecting a cell once. For example, a population of GP+E-86JZenCD24tkneo viral producer cells and lacking in wild-type virus is prepared by infecting ecotropic retroviral packaging cells (GP+AM12) with JZenCD24tkneo. Other examples of packaging cell lines which may be used to prepare viral producer cells are ζ2 cells (Mann, R. et al., Cell, 23;153–159, 1983) and PA317 (Miller, A. D. et al., Somatic Cell. Mol. Genet. 12:175, 1986) PA 317 (Miller, A. D. and Buttimore C., Mol. Cell. Biol. 6:2895, 1986).

The viral producer cell may be used to infect a selected cell. This may be achieved by co-culturing the viral producer cell with the selected cell. For example, bone marrow cells from adult mice can be infected with JZenCD24tkneo by coculturing with irradiated GP+E-86JZenCD24tkneo viral producer cells for 24 hours.

As hereinbefore mentioned the invention further provides a method of identifying a cell and progeny thereof comprising: providing a cell; infecting the cell with a recombinant viral vector of the invention under suitable conditions to allow expression of the cell surface protein on the cell; and, identifying the cell and progeny thereof by detecting expression of the cell surface protein on the cell or progeny thereof.

The method of the invention may be used to identify a particular cell, population of cells, and cells in a cell line, and progeny thereof. Progeny of a cell includes any cells which derive from the particular cell, for example mitotic progeny arising from cell division. The progeny may be phenotypically diverse.

In a preferred embodiment, the cell is a hemopoietic cell, preferably a totipotent hemopoietic stem cell capable of regenerating a wide array of myeloid and lymphoid cell types. Hemopoietic stem cells may be obtained from bone marrow or peripheral blood of a donor. A sample of hematopoietic cells may be pre-treated prior to infecting with the recombinant viral vector of the invention to enrich primitive leukemic hematopoietic stem cells in the sample. Red blood cells may be removed from the sample, for example by a brief exposure to ammonium chloride. For blood cell samples, a preparation of light density cells (for example $<1.077$ gm/cm$^3$) may be isolated by centrifugation on Ficoll-Hypaque. The sample may also be depleted of T cells for example, where the initial cell sample is obtained from the blood of a mammal without an elevated white blood cell count. T cell depletion may be effected, for example by incubation of the light density cells with 2-aminoethylisothiouronlum bromide-treated sheep erythrocytes for 30 minutes on ice followed by further centrifugation to remove the rosetted T cells as described generally by Marsden et al., J. Immunol. Methods, Vol. 33, p. 323, 1980. T cell removal prevents the spontaneous activation and outgrowth in vitro of Epstein-virus transformed B lymphocytes.

The cell is infected with a recombinant viral vector of the invention. It is preferred that the recombinant viral vector has a nucleotide sequence encoding a cell surface protein having substantial homology to the nucleotide sequence encoding CD24, of a different animal species than the cell to be infected. For example, if the selected cell is from a human, the recombinant viral vector has a nucleotide sequence encoding murine M1/69-J11d heat stable antigen. If the selected cell is a murine cell, the recombinant viral vector has a nucleotide sequence encoding human CD24.

The cell is infected with a recombinant viral vector of the invention under suitable conditions to allow expression of the cell surface protein on the recombinant cell. The cells may be infected by co-culturing with viral producer cells as described above. Conditions suitable for expressing the cell surface protein will depend on the nature of the viral vector and the host to be infected.

Cells and progeny thereof expressing the cell surface protein may be detected using a substance which is capable of binding to the cell surface protein. For example, labelled antibodies may be used to detect the cells and progeny thereof. The antibodies may be coupled to a detectable substance. Detectable substances include various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include radioactive iodine $^{125}$I, $^{131}$I, 35S or tritium.

The substance capable of binding to the cell surface protein may be insolubilized. For example, antibodies against the cell surface protein may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ethermaleic acid copolymer, amino acid copolymer, ethylene-maleic acid copolymer, nylon, silk, etc. The carrier may be in the shape of, for example, a tube, test plate, beads, disc, sphere etc.

The insolubilized antibodies may be prepared by reacting the antibodies with a suitable insoluble carrier using known chemical or physical methods, for example, cyanogen bromide coupling.

Bispecific antibodies capable of binding to the cell surface protein coupled to a detectable substance may also be used to detect the cells and progeny thereof expressing the cell surface protein. The bispecific antibody may be capable of binding to the cell surface protein and to a detectable substance as described above.

The bispecific antibody may be prepared using procedures known in the art such as disclosed in Staerzt and Bevan (1986 PNAS (USA) 83:1453; 1986 Immunology Today 6;241). In general, a hybrid hybridoma is formed from a fusion between a first cell line which produces a first monoclonal antibody which is capable of binding to the cell surface protein and a second cell line which produces a second monoclonal antibody which Is capable of binding to a detectable substance. They may also be constructed by chemical means using procedures such as those disclosed by Staerz et al., ((1985) Nature 314:628) and Perez et al., (1985, Nature, 316:354)

Tetrameric immunological complexes may also be used to detect the cells and progeny expressing the cell surface protein. The complexes comprise a first monoclonal antibody which is capable of binding to the cell surface protein and a second monoclonal antibody which is capable of binding to a detectable substance wherein the first and second antibody are from a first animal species, conjugated to form a cyclic tetramer with two monoclonal antibodies of a second animal species directed against the Fc-fragment of the antibodies of the first animal species.

The tetrameric immunological complex may be formed by reacting a first monoclonal antibody which is capable of binding to the cell surface protein and a second monoclonal antibody which is capable of binding to a detectable substance wherein the first and second antibody are from a first animal species, with an about equimolar amount of antibodies of a second animal species which are directed against the Fc-fragments of the antibodies of the first animal species and isolating the tetrameric complex formed. (See U.S. Pat. No. 4,868,109 to Lansdorp for a description of tetrametic antibody complexes and methods for preparing them).

Preferred antibodies that may be used to detect cells and progeny expressing the cell surface protein include antibodies specific against CD24 such as anti-CD24 antibody 32012 (Stremer Finderaol, Oslo Norway)

The appropriate method of detecting cells expressing the cell surface protein and labelled with a detectable substance is dependent upon the detectable substance chosen. For example, if the detectable substance is an enzyme, the labelled cells can be determined by measuring the enzymatic activity using a proper enzyme substrate for colorimetric, luminescent or fluorescent systems. If the detectable substance is a fluorescent material, labelled cells can be determined by measuring fluorescence intensity, and if the detectable substance is a radioactive material, the metastatic potential can be determined by measuring the radioactivity.

In a preferred method for detecting cells expressing CD24, a tetramolecular antibody complex is used which contains antibodies having specificity against CD24, R phycoerythrin and the F(ab)2 fragment of IgG. Following incubation the cells expressing CD24 antigen were labelled with R-phycoerythrin and analysed on a FACStar+ (Beckton Dickinson and Co., San Jose, Calif.).

The labelled cells expressing cell surface protein may be further characterized. For example, labelled hemopoietic cells may be used to initiate long term cultures, by the methods described in Eaves et al., J. Tissue Culture Methods, Vol. 13, p. 55, 1991. The clonogenic progenitor cells resulting from long term culture may be assayed for clonogenic erythropoietic (BFU-E), granulopoietic (CFU-GM), and multilineage (CFU-GEM) progenitors.

The cell and progeny thereof identified using the methods of the invention may be isolated using techniques known in the art to provide an enriched preparation of cells.

In an embodiment of the invention the recombinant viral vector additionally comprises an exogenous gene and expression control sequences operatively linked thereto and the method of the invention is used to monitor exogenous gene expression. In particular a method is provided for monitoring exogenous gene expression in a cell and in progeny thereof comprising: providing a cell; infecting the cell with a recombinant viral vector having an exogenous gene and one or more expression control sequences operatively linked thereto, and a nucleotide sequence encoding a cell surface protein and having substantial homology to the nucleotide sequence encoding CD24 and one or more regulatory elements operatively linked thereto, under suitable conditions to allow expression of the exogenous gene and the cell surface protein in the cell and; identifying the cell and progeny thereof expressing the exogenous gene by detecting cells expressing the cell surface protein. In a preferred embodiment the cell is a hemopoietic cell. Examples of exogenous genes which may be monitored are described in detail above. The expression of the exogenous gene may be quantitated by quantitating the expression of the cell surface antigen.

Cells infected with a recombinant viral vector of the invention as described above may be transplanted into a host, and the cell and progeny thereof may be identified after transplantation by removing samples from the host, and assaying for cells expressing CD24. The infected cells may be transplanted using conventional methods into the same (allogenic transplantation) or different host (autologous transplantation). A recombinant viral vector of the invention may also be directly introduced into a host to infect the host's cells in vivo. Hosts which may be transplanted using the methods of the invention include avian, mammalian, and other animals.

In an embodiment of the method, the infected cell is a hemopoietic cell and the hemopoietic system of the host is ablated prior to transplant, for example by total body irradiation or by cytotoxic drugs, such that the hemopoietic system of the host may be reconstituted by cell lineages derived from the infected cell. Thus, the efficacy of bone marrow transplants in the treatment of a variety of conditions such as AIDS, leukemia and certain anemias, and in gene therapy, may be assessed using the method of the invention by determining the number and characteristics of primitive hematopoietic leukemic stem cells expressing the cell surface protein at time periods after treatment.

Cells may be identified in samples removed from the transplanted host. Suitable samples include tissue samples, such as thymus, spleen or lymphoid tissue or cell suspensions from bone marrow or peripheral blood.

The recombinant viral vector may contain an exogenous gene encoding a biologically active protein which is selected to modify the genotype and phenotype of the cell to be infected. For example, the exogenous gene may be selected for gene augmentation to modify the expression of mutant genes in the cell, to restore genetic function by introducing the exogenous gene into non-specific sites in the cell's genome. The expression of the exogenous gene may be quantitated by measuring the expression levels of the cell surface protein in infected cells.

Cells infected with recombinant viral vectors of the invention transplanted into a host may be used to introduce an exogenous gene coding for a biologically active protein which corrects or compensates for a genetic deficiency. Examples of such genetic deficiencies include hereditary or acquired genetic defects, such as hemophilia, anemia, cancer including leukemia, cystic fibrosis, and thalassemia. The expression of the exogenous gene in the host can be monitored by detecting and quantitating the expression of the cell surface protein on cells from samples removed from the host. In the case of cystic fibrosis, the normal cystic fibrosis conductance regulator may be introduced into epithelial cells derived, for example, from the airways of a mammal to correct the $Cl^-$ transport defect in the cells.

The method of the invention may also be used to study development of cells such as the development of cells of the hemopoietic lineage. For example, cells infected with a recombinant viral vector of the invention can be transplanted into hosts of different genetic backgrounds and the fate of the cells can be followed by detecting cells expressing the cell surface protein.

Recombinant viral vectors of the present invention may also be used to induce host tolerance to autologous transplants. For example, transplantation tolerance to autologous bone marrow cells may be induced by introducing an allogeneic major histocompatability (MHC) antigen into the autologous cells. Expression of the MHC antigen in the host may induce donor-specific tolerance. Accordingly, the exogenous gene in the recombinant viral vector of the present invention may be an MHC antigen allogeneic in respect to the cell to be infected. Cells, preferably hemopoietic stem cells, infected with a viral vector expressing an allogeneic MHC antigen may be transplanted into an ablated host to repopulate the hemopoietic system and to induce donor-specific tolerance to the chimeric cells.

The invention will be more fully understood by reference to the following examples. However, these examples are merely intended to illustrate embodiments of the invention and are not to be construed to limit the scope of the invention.

EXAMPLES

The following materials and methods were utilized in the investigations outlined in the examples.

Animals

Animals used in these experiments were 8 to 12 week old (C57B1/6J×C3H/HeJ)F1 (B6C3F1) male and female mice bred and maintained in the animal facility of the British Columbia Cancer Research Centre from parental strain breeders originally obtained from the Jackson Laboratories, Bar Harbour, Mass. Donor mice used for competitive repopulation experiments were 10 to 14 week old male or female (C57B1/6Ly-Pep3b×C3H/HeJ)F1 (PepC3F1).

Retroviral Vectors

All experiments utilized a retroviral based vector originally constructed from Jzen1, a retroviral backbone provided by Dr. S. Cory (Walter and Eliza Hall Institute, Melbourne, Australia). The 3' LTR of Jzen1 is derived from the myeloproliferative sarcoma virus (Johnson et al., EMBO J. 8:441, 1989). To construct JZenCD24tkneo, a 310 bp Sal I fragment containing only the coding region of the CD24 gene as described in Kay et al (1991, J. Immunol. 147:1412) was removed from PAX114 and inserted into the Xho I site of Jzentkneo using standard procedures. Jzentkneo was constructed by inserting a 1092 bp Sma I- HindIII fragment from PTZ19RTKNEO harbouring the $neo^R$ gene under the regulatory control of a mutant polyoma virus enhancer tandem repeat and the Herpes Simplex Virus thymidine kinase gene promoter into a Hpa I-HindIII digested Jzen1.

Cell Lines

The ecotropic packaging cell line GP+E-86 and the amphotropic cell line GP+AM12 as described in Markowitz at al. (J. Virol. 62:1120, 1988) were used to generate helper free recombinant retrovirus. The cell lines were maintained in HXM medium, composed of Dulbecco's Modified Eagles Medium (DMEM; Stem Cell Technologies, Vancouver, B.C.), 10% heat inactivated (55° C. for 30 minutes) newborn calf serum (Gibco/BRL Canada; Burlington, Ontario, Canada), hypoxanthine (15 ug/ml; Sigma Chemical Co.), xanthine (250 ug/ml; Sigma Chemical Co., St. Louis, Mo.), and mycophenolic acid (25 ug/ml; Sigma). Viral packaging cells were maintained in HXM medium supplemented with 1 mg/ml of the neomycin analogue G418 (Gibco/BRL Canada). All cells were cultured at 37° C. in an atmosphere of 5% CO2.

Retrovirus Production

GP+AM12 amphotropic retroviral packaging cells were first transfected with the JZenCD24tkneo retroviral vector using calcium phosphate precipitation. Supernatant from these cells was then used to infect GP+E-86 ecotropic retroviral packaging cells infected cells were selected in 1 mg/ml G418 to obtain a polyclonal population of GP+E-86JZenCD24tkneo viral producer cells. Viral titre was determined to be $5 \times 10^5$ CFU/ml based on transfer of G418 resistance to NIH 3T3 fibroblasts. Absence of helper virus was verified by failure to serially transfer virus conferring G418 resistance to NIH 3T3 cells.

Virus Infection of Marrow Cells

Bone marrow cells from adult male or female B6C3F1 or PepC3F1mice injected 4 days previously with 150 mg of 5-fluorouracil per kg body weight were flushed from femoral shafts with alpha medium and 5% FCS. Marrow cells were suspended by repeated passage through a 21 gauge needle and nucleated cell counts were performed using a hemocytometer chamber. Cells were infected using a coculture infection protocol in which $3 \times 10^6$ marrow cells were cultured on top of irradiated (1500 Cgy X-rays) GP+E-86JZenCD24tkneo viral producer cells for 24 to 48 hours in medium composed of DMEM, 15% FCS (Sigma), 10 ng/ml human IL-6, 6 ng/ml murine IL-3, 100 ng/ml murine Steel factor and 7 $\mu$g/ml polybrene. Cells used for competitive repopulation experiments were first prestimulated for 48 hours in the above medium in the absence of polybrene prior to infection. Loosely adherent and non-adherent cells were recovered by gentle agitation and washing of dishes. Cells were pelleted, resuspended in fresh culture medium and incubated for a further 48 hours (or as indicated) at 37° C. to allow expression of the transferred CD24 gene.

Labelling of Cells

Cells were recovered from culture, washed once in alpha medium/5% FCS, resuspended (1 to $7 \times 10^6$ cells/ml) in 200–400 μl of medium conditioned by hybridoma 2.4G2 (Unkeless, J. C., 1979, J. Exp. Med. 150:580) which secretes an anti-murine-IgG Fc receptor antibody, and incubated on ice for 30 minutes. Cells were then washed once with Hank's balanced salt solution containing 2% FCS and 0.1% sodium azide (HFN). A tetramolecular complex of monoclonal antibodies used for the staining procedure was prepared by combining anti-CD24 antibody 32D12 (from Stemer Finderaol, Oslo, Norway), anti-R phycoerythrin antibody ID3, and the F(ab)$_2$ fragment of the anti-IgG antibody P9. Cells were incubated on ice for 40 minutes, washed twice with HFN, and then stained with R-phycoerythrin. After a further 40 minutes on ice, cells were washed twice with HFN and resuspended in HFN containing 1 μg/ml of 7-amino actinomycin D (7AAD) from Sigma to distinguish dead cello. Bone marrow cells cultured on GP+E-86 packaging cells, or cells infected with a Jzen-neo virus were used as negative controls.

FACS Sorting

Cells were sorted on a FACStar+ (Beckton Dickinson and Co., San Jose, Calif.) equipped with a 5 W argon and a 30 mW helium neon laser. Cells were collected in sterile eppendorf vials in alpha medium/50% FCS.

Progenitor Assay

Sorted and unsorted bone marrow cells were plated in 35 mm petri dishes (Greiner, Germany) in 1.1 ml culture mixtures containing 0.8% methylcellulose in alpha medium supplemented with 30% FCS, 1% bovine serum albumin (BSA), $10^{-4}$M β-mercaptoethanol, 3 U/ml partially purified human urinary erythropoietin (Stem Cell Technologies, Vancouver, B.C.), 2% pokeweed mitogen stimulated mouse spleen cell conditioned medium (PWM-SCCM; Stem Cell Technologies), and 10% agar stimulated human leukocyte conditioned medium (LCM; Stem Cell Technologies). Cells were plated in the presence or absence of 1.5 mg/ml of G418 (Gibco/BRL Canada). Colonies >20 cells were counted after 8 days incubation at 37° C. in an atmosphere of 5% $CO_2$.

Spleen Colony Assay

Irradiated male or female B6C3F1 mice (910–950 Cgy, 110 cGy/min, $Cs^{137}$) were injected intravenously with $1\times10^3$ to $1\times10^4$ cells from the appropriate cell fraction. On day 12 animals were sacrificed via cervical dislocation and well isolated macroscopic spleen colonies were dissected for FACS and DNA analysis.

Competitive Repopulating Unit Assay

Limiting numbers of sorted or unsorted Ly5.1/Ly5.2 (PepC3F1) bone marrow cells were injected into lethally irradiated (930 Cgy, $Cs^{137}$) B6C3F1(Ly5.2) recipients in combination with $2\times10^5$ "compromised" Ly5.2 marrow helper cells. These compromised cells contain approximately normal numbers of CFU-S and in vitro clonogenic progenitor cells, but have been seriously compromised in their competitive long term repopulating ability by subjecting them to two previous rounds of serial transplantation and regeneration (Harrison, D. E. et al., 1978, J. Exp. Med. 147:1526). Reconstitution of recipients with donor cells was assessed at 5–6 weeks post transplantation by analysis of peripheral blood samples (50–100 μl) obtained by tail vein puncture. Samples were depleted of erythrocytes by incubating them for 10 minutes on ice in the presence of 4 volumes of sterile 1M NH4Cl solution. Cells were then stained with an FITC-conjugated anti-Ly5.1 Mab (hybridoma A20-1.7 provided by G. Spangrude) and analyzed on a FacScan cell analyzer (Becton Dickinson and Co.). Similarly, levels of expression of the transferred CD24 gene were analyzed by staining peripheral blood samples with the 32D12 based tetramolecular Mab complex and R-phycoerythrin as described above.

Competitive repopulated animals used for quantitation of gene expression and phenotypic analysis of CD24 positive cells were injected with $5\times10^6$ retrovirally infected PepC3 cells following culture for 11 days in the presence of IL-6, IL-3, Steel factor and FCS. These mice were also injected with $2\times10^5$ compromised helper cells. Hemopoietic reconstitution of these animals was assessed at 6 weeks and 4 months post transplantation. Phenotypic FACS analysis of peripheral blood samples was performed using a double antibody labelling technique; anti-CD24 antibody in combination with one of Gr.-1 to identify granulocytes, Mac-1 for macrophages, Ly-1 for T cells or B220 for B cells.

DNA Analysis

DNA was purified from NaDodSO4/proteinase K digested cells by phenol/chloroform extraction (Maniatis, T. at al., 1982, Molecular Cloning; a Laboratory Manual (Cold Spring Harbor Lab., Cold Spring Harbor, N.Y.). DNA was dialyzed for 24 hours against 1× TE buffer and digested with Xba I or Eco RI (BRL) at 37° C. for 12–16 hours. Following ethanol precipitation, DNA was dissolved in 20 μl of Lx TE buffer, electrophoresed through a 0.8% TAE agarose gel for 16–20 hours at 30 volts, and transferred to a nylon (Zeta-Probe; Bio-Rad) membrane. Blots were subsequently probed using a fragment of the neoR gene (from plasmid pMC1neo) labelled to high specific activity with $^{32}$P.

The CD24 Cell Surface Protein

The JZenCD24tkneo retroviral vector used in these studies is shown in FIG. 1. The vector contains the coding portion of the CD24 cDNA under the control of the myeloproliferative sarcoma virus long terminal repeat enhancer and promoter regulatory elements. In addition, a neomycin resistance gene regulated by the Herpes Simplex Virus thymidine kinase gene promoter and a mutant polyoma virus enhancer has also been included in the vector.

Example 1

Infection of Hemopoietic Cell Lines

Figure 2A:
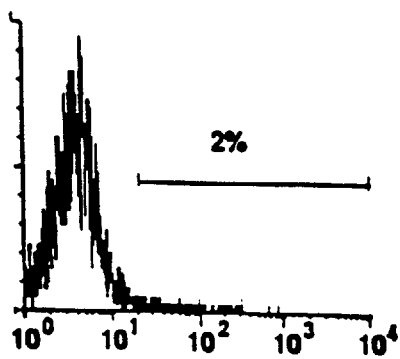
FIG. 2 shows the FACS profiles for uninfected BAF-3 cells (A) and BAF-3 cells infected with JZenCD24tkneo virus (B)
Figure 2B:
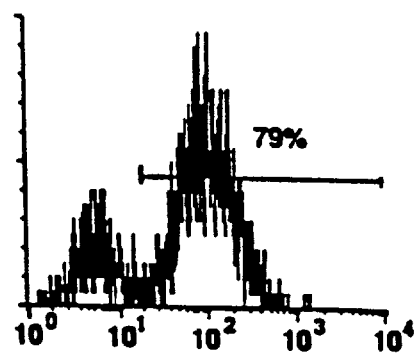

To test the feasibility of utilizing cell surface proteins as dominant selectable markers in retroviral mediated gene transfer, the CD24 recombinant retrovirus, described above was first used to infect the hemopoietic based pre-B cell line BA/F3. BAF-3 cells were infected by co-culturing with JZenCD24tkneo viral producer cells for 48 hours and subsequently cultured for 5 days in the absence of G418 selection. Cells were then stained with an anti-CD24 based tetramolecular Mab complex and analyzed by FACS. Approximately 80% of recovered cells expressed high levels of the CD24 cell surface protein as compared to uninfected cells stained with the same Mab complex. The results are shown in FIG. 2. The graphs shown in FIG. 2 are FACS profiles for uninfected BAF-3 cells (A) and BAF-3 cells infected with the JZenCD24tkneo virus (B). The maximum levels of CD24 expression in infected BAF-3 cells were achieved within a minimum of 12 hours following termination of culture with the viral producers.

Example 2

Infection and Selection of Primary Murine Bone Marrow Cells

Figure 3A:
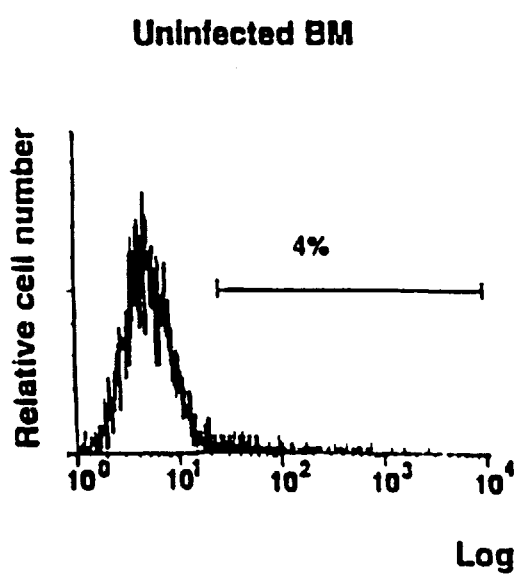
FIG. 3 is a FACS profile showing the expression of the transferred CD24 in primary marrow cells.
Figure 3B:
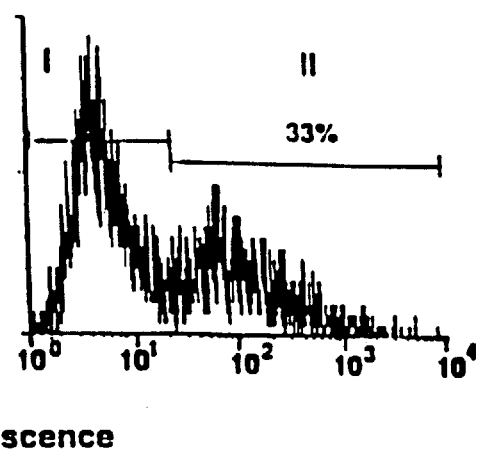

Day 4 5-FU bone marrow cells were co-cultivated with viral producer cells for 24 hours in the presence of 7 μg/ml of polybrene. Cells were subsequently cultured for an additional 48–72 hours to allow for expression of the transferred CD24 cDNA. A time course experiment performed on infected day 4 5-FU marrow determined that maximal levels of CD24 expression are achieved within 48–72 hours following termination of the infection procedure (data not shown). The FACS profiles of cells stained with the antiCD24 mAb complex are shown in FIG. 3. The FACS profiles in FIG. 3 show that the transferred CD24 gene was expressed in primary bone marrow cells within 48 hours following infection. In particular FIG. 3 shows that 26% of the cells exposed to the JZenCD24tkneo retrovirus are stained positive for the presence of the CD24 antigen.

Figure 4:
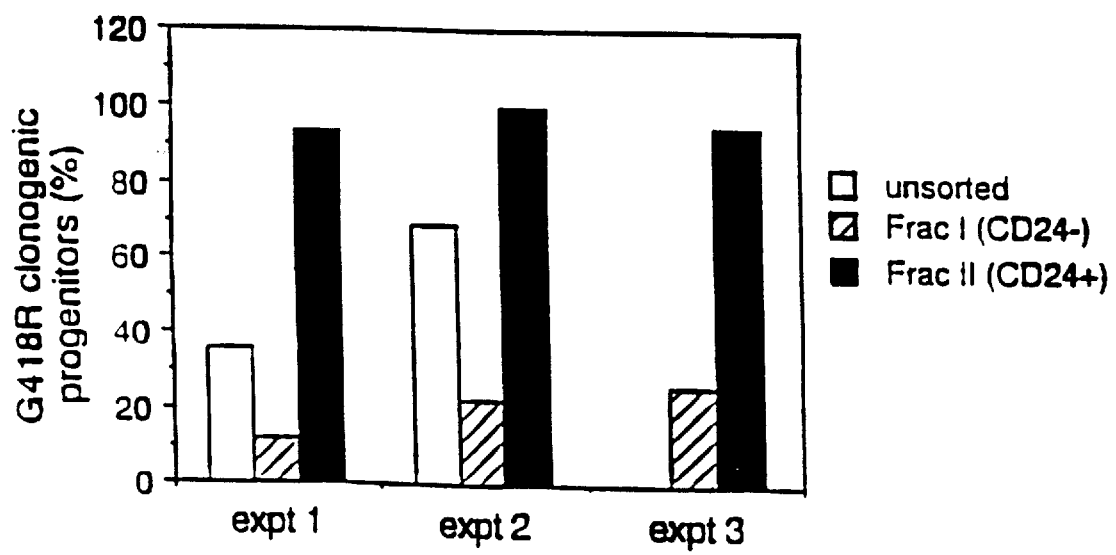
FIG. 4 is a bar graph showing the proportion of neomycin resistant CFU-C in each of 3 sorted fractions.

Using FACS, cells were separated into two fractions; a negative fraction (I), a positive fraction (II). A portion of bone marrow cells from each of the two fractions and unsorted cells were then placed into methylcellulose semi-solid medium in the presence or absence of the neomycin analogue G418 to determine what proportion of the cells from each fraction were neomycin resistant. FIG. 4 shows the proportion of neomycin resistant CFU-C in each of the fractions and unsorted cells. An unsorted fraction was not obtained in experiment 3 due to a lack of cells. The results, shown in FIG. 4, reveal that while only 35–69% of CFU-C from the unsorted cells were neomycin resistant the vast majority (ie. >93%) of CFU-C from the CD24 positive fraction were able to survive and grow in the presence of G418.

Figure 5:
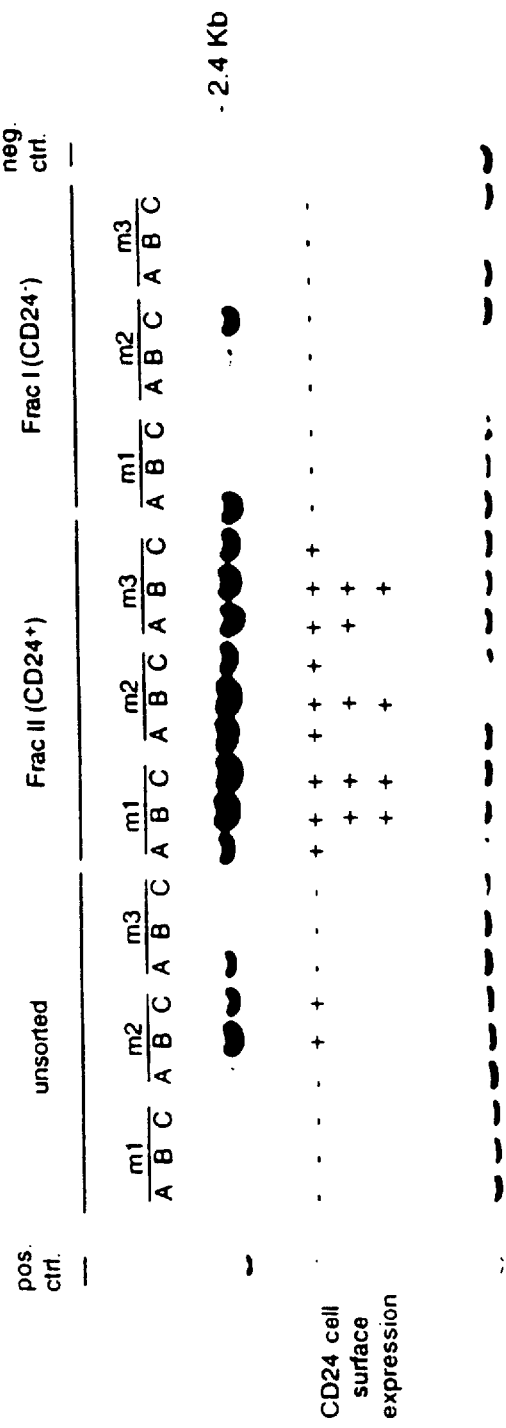
FIG. 5 shows an autoradiograph of a Southern blot showing the presence of provirus among various individual spleen colonies (A) and an autoradiogram of the same blot probed with a fragment from the single copy erythropoietin receptor gene to ensure equal loading of DNA(B)

In addition to the analysis of in vitro clonogenic progenitors the CFU-S within each fraction was also studied. Typically, lethally irradiated recipients were injected with 4,000 to 5,000 bone marrow cells from one of each of the two fractions or unsorted cells. Twelve days later recipients were sacrificed and well isolated spleen colonies were collected for both FACS and Southern analysis. Table 1 shows the total number of colonies that were analyzed from each of the two sorted fractions and unsorted cells as well as the number of colonies that were concluded to be positive for provirus on the basis of either FACS or Southern analysis. A colony was concluded to be positive by FACS if greater than 5% of the population was found to express the CD24 antigen. All spleen colonies derived from cells selected by FACS on the basis of CD24 expression were found to be positive for provirus. In addition, approximately 50% of the colonies derived from both unsorted cells and negative fraction CFU-S were marked with provirus as shown in FIG. 5. FIG. 5A is an autoradiograph of a Southern blot showing the presence of provirus among various individual spleen colonies. DNA was digested with Xba I, an enzyme that cuts once within each proviral LTR as well as once within the CD24 CDNA. The blot was probed with a $^{32}P$ labelled fragment from the neomycin resistance gene. The numbers below each lane represent the proportion of cells from each colony that were found to be expressing the transferred CD24 gene. FIG. 5B shows the same blot probed with a fragment from the single copy erythropoietin receptor gene to ensure equal loading of DNA among the lanes.

Although a number of colonies derived from negative fraction and unsorted CFU-S were marked with provirus, in some cases quite strongly, very few of them were found to be expressing significant levels of the CD24 antigen as determined by FACS analysis; only 13% of clones from the unsorted cells and 12% of clones from the CD24 negative fraction were found to be expressing significant levels of the CD24 antigen. In contrast all colonies derived from CFU-S sorted initially for CD24 expression were found to express significant levels of the CD24 cell surface protein. A correlation between proviral copy number and the level of CD24 expression was observed. Southern blot analysis of EcoR1 digested spleen colony DNA to release the proviral integrant revealed that colonies derived from CD24 positive CFU-S had in general 4 or more proviral copies per clone while CD24 negative CFU-S had fewer than 4 copies of provirus per clone.

Figure 6A:
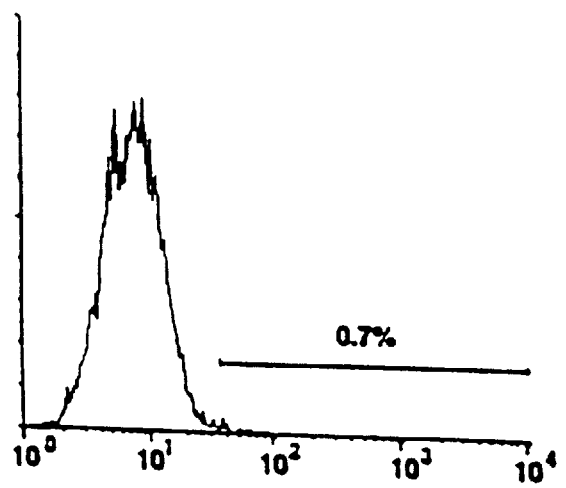
FIG. 6 is a FACS profile showing the expression of the transferred CD24 gene in primary bone marrow cells in negative fractions (I), or fractions positive for CD24 expression (II)
Figure 6B:
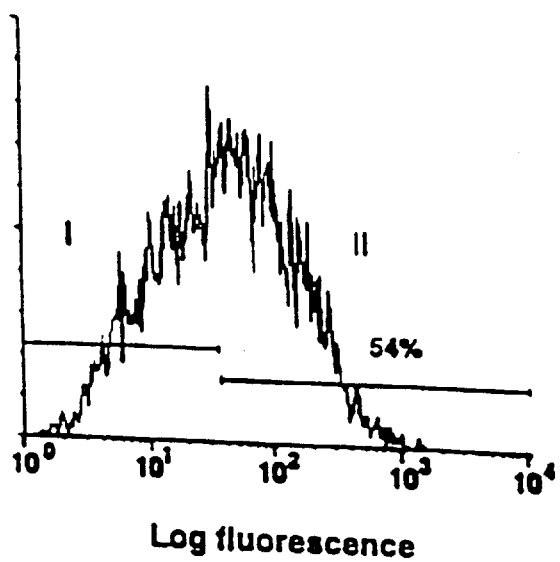
Figure 7G:
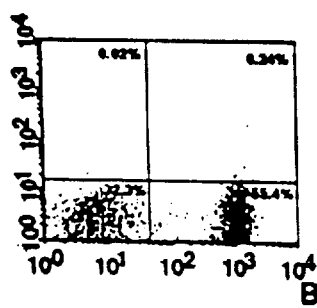
FIG. 7 are FACS profiles showing expression of the transferred CD24 gene in peripheral blood cells of mice 4 months following transplantation with bone marrow infected with JZenCD24tkneo virus (mouse D) or the control virus JZen neo (control)
Figure 7H:
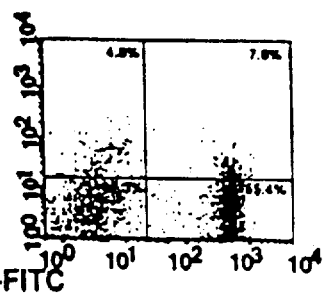
Figure 7I:
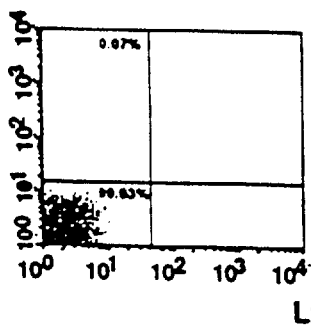
Figure 7J:
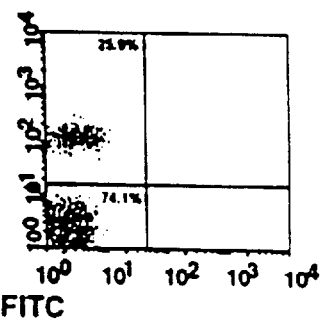

To determine if cells capable of competitive repopulation of a lethally irradiated recipient could also be selected, day 4 5-FU bone marrow was co-cultured for 2 days in the presence of JZenCD24tkneo viral producer cells following a 48 hour period of prestimulation. Cells were then cultured for a further 2 days to allow the expression of the transferred CD24 gene. FACS profiles of cells infected with either a JZenneo control virus (left) or the JZenCD24tkneo virus (right) are shown in FIG. 6. Cells were sorted into 3 fractions; a CD24 negative fraction (I), a CD24 positive fraction (II) and unsorted cells. Following the sorting procedure either $1\times10^4$ or $4\times10^4$ cells from one of each of the fractions and unsorted cells was injected into irradiated recipients along with $2\times10^5$ compromised helper cells via the tail vein. Hemopoietic reconstitution of recipients with donor cells was assessed at 5 weeks post transplantation. Previous results obtained using this competitive repopulating unit (or CRU) assay have revealed that when limiting numbers of CRU were injected into recipients, the readout of these cells was similar whether recipients were analyzed at 5 weeks or 7 months post transplantation.

The results support the conclusion that, using this assay, cells with long term competitive repopulating ability can be readout as quickly as 5 weeks following transplantation. Table 2 shows the results of FACS analysis of peripheral blood samples from 21 of 27 recipients receiving cells from the negative, positive or unsorted fractions. Both the proportion of Ly5. 1+ donor derived cells and the proportion of peripheral blood cells expressing the CD24 cell surface protein were determined. Of 11 recipients receiving cells from the CD24 positive fraction, 8 showed >20% donor derived repopulation and 10 of the 11 animals showed >5% of their peripheral blood cells expressing the CD24 antigen.

Southern analysis of DNA obtained from bone marrow and thymus from these animals, as shown in FIG. 7, revealed retroviral marking in 10 of 11 animals. FIG. 7 shows FACS profiles showing expression of the transferred CD24 gene in peripheral blood cells of mice 4 months following transplantation with bone marrow infected with JZenCD24tkneo virus (mouse D) or the control virus JZen neo (control). Cells were stained with antibody to CD24 and antibody specific to granulocytes (GR-1), macrophages (Mac-1), B-lymphocytes (B220), T-lymphocytes (Ly-1) or erythroid cells (Ter11). Three animals harboured common proviral integration sites in both myeloid and lymphoid tissues indicative of gene transfer to a totipotent stem cell. Of 11 animals repopulated with cells from the CD24 negative fraction, 8 showed >20% donor derived repopulation. However, in contrast to animals receiving CD24 positive cells none of the 11 animals given CD24 negative cells were found to express significant levels (ie. >5% of peripheral blood cells) of CD24 despite the detection of provirus in either the bone marrow, thymus, or both tissues in 9 of the recipients. Of 5 recipients receiving cells from the unsorted fraction all showed >20% donor repopulation and 2 had >5% of their peripheral blood cells expressing the CD24 antigen although all 5 showed retroviral marking in the myeloid and/or lymphoid tissues.

Example 3

Detection and Quantification of Gene Expression in Competitively Repopulated Mice To test whether the CD24 cell surface protein could be used as a means to rapidly detect and quantitate gene expression in vivo, lethally irradiated Ly5.2 B6C3F1 hybrid mice were reconstituted with retrovirally infected Ly5.1/Ly5.2 histocompatible bone marrow from PepC3F1 donors following 11 days in culture and analyzed 6 weeks and 4 months post transplantation.

Peripheral blood samples were taken from each of 10 recipients at 6 weeks post transplantation and analyzed by FACS using antibodies directed against the Ly5.1 and CD24 cell surface proteins. Of the 10 animals, 9 showed >45% donor derived repopulation. The proportion of peripheral blood cells expressing the CD24 antigen ranged from 5–38%. Two of the animals, C and D, showing a high proportion of CD24+ peripheral blood cells, 26% and 17% respectively, were sacrificed at 4 months post transplantation and the peripheral blood, bone marrow, spleen and thymus were analyzed by flow cytometry using antibodies recognizing Ly5.1 and CD24 (Table 3). Interestingly, the proportion of peripheral blood cells expressing the CD24 antigen in recipient C increased from 26% at 6 weeks post transplantation to 41% at 4 months post transplantation while the proportion of CD24+ cells in animal D and the proportion of Ly 5.1+ cells in both animals remained the same. In addition, the peripheral blood and bone marrow cells from these two animals were subjected to double staining procedures to determine which hemopoietic lineages were expressing the transferred CD24 gene. The proportion of CD24 positive cells in the bone marrow of mouse C is greater than the proportion of Ly 5.1 donor cells since the CD24 antigen can remain on the surface of mature red blood cells produced by retrovirally infected erythroid precursors. Ly 5.1 is not found on mature red blood cells.

The FACS profiles shown in FIG. 7 reveal that all the hemopoietic cell lineages tested were found to express the CD24 antigen including granulocytes, macrophages, and to a lesser extent B and T lymphocytes. In addition, by staining bone marrow cells with the antibody Ter119 which recognizes an antigen expressed on proerythrocytes, we determined that this cell type also expressed the CD24 antigen. Mature red blood cells were also found to harbour the CD24 antigen on the cell surface.

Having illustrated and described the principles of the invention in a preferred embodiment, it should be appreciated by those skilled in the art that the invention can be modified in arrangement and detail without departure from such principles. We claim all modifications coming within the scope of the following claims. In addition, reference is made herein to various publications which are hereby incorporated by reference in their entirety.

TABLE 1

Southern and FACS Analsis of Individual Spleen Colonies Derived from Sorted and Unsorted CFU-S

| fraction | #colonies analyzed | #colonies positive (FACS) | #colonies positive (Southern) |
| --- | --- | --- | --- |
| unsorted | 30 | 4 | 13 |
| positive | 37 | 37 | 37 |
| negative | 26 | 3 | 15 |

Individual spleen colonies were isolated 12 days post injection from lethally irradiated mice given 4000–5000 bone marrow cells from one of each of the 3 sorted fractions. Each spleen colony was dissected and analyzed using both FACS and Southern analysis. A colony was concluded to be positive by FACS if greater than 5% of the population was found to express the CD24 antigen. The table shows data accumulated over three separate experiments.

TABLE 2

FACS Selection of CRU 2 Days Post Infection of Day 4 5-FU Bone Narrow with CD24 Retrovirus

| | Sorted Cells Assayed for Competitive Repopulating Units | |
| --- | --- | --- |
| | Fraction I | Fraction II |
| No. of Mice with Donor Repopulation >20% | 8/11 | 8/11 |
| No. of Mice Reconstituted with Retrovirally Marked Cells (detected by Southern analysis) | 6/11 | 10/11 |
| No. of Mice with >5% CD24 Expressing Peripheral Blood Cells (detected by FACS) | 0/11 | 10/11 |

TABLE 3

| mouse/tissue | proportion Ly 5.1 + cell (%) | proportion CD24 + cells (%) |
| --- | --- | --- |
| C/p.b. | 85 | 41 |
| C/BM | 59 | 80 |
| C/spleen | 48 | 40 |
| C/thymus | 87 | 55 |
| C/p.b. | 88 | 17 |
| C/BM | 47 | 25 |
| C/spleen | 57 | 9 |
| C/thymus | 89 | 8 |

Proportion of Ly5.1 and CD24 positive cells in various hemopoietic tissues of completely repopulated mice C and D 4 months post transplantation. The proportion of CD24 positive cells in the bone marrow of mouse C is greater than the proportion of Ly5.1 donor cells since CD24 antigen can remain on the surface of mature red blood cells produced by retrovirally infected erythroid precursors. Ly 5.1 is not found on mature red blood cells.

I claim:

1. A method of marking a hemopoietic cell and progeny thereof comprising introducing in vitro into a hemopoietic cell of a mammal a recombinant retroviral vector comprising a nucleic acid molecule having a sequence encoding a protein which is not native to the mammal and having the nucleotide sequence of CD24 as shown in the Sequence Listing as SEQ ID No:1 or having a nucleotide sequence encoding the murine M1/69-J11d heat stable antigen as shown in the Sequence Listing as SEQ ID NO:2 under suitable conditions to allow expression of the protein on the surface of the hemopoietic cell or progeny thereof.

2. A recombinant retroviral vector having a nucleotide sequence encoding CD24 as shown in the Sequence Listing as SEQ ID No:1 and a nucleotide sequence encoding an exogenous gene.

3. A recombinant retroviral vector according to claim 2 wherein said vector is JzenCD24tKneO.

4. A recombinant retroviral vector having a nucleotide sequence encoding the murine M1/69-J11d heat stable antigen as shown in the Sequence Listing as SEQ ID NO:2, and a nucleotide sequence encoding an exogenous gene.

5. A method of identifying a human hemopoietic cell and progeny thereof comprising infecting in vitro the hemopoietic cell with a recombinant retroviral vector as claimed in claim 4 under suitable conditions to allow expression of the murine M1/69-J11d heat stable antigen and identifying the cell and progeny thereof by detecting expression of murine M1/69-J11d heat stable antigen on the hemopoietic cell or progeny thereof.

6. A method for monitoring exogenous gene expression in a human hemopoietic cell and in progeny thereof comprising infecting in vitro the hemopoietic cell with a recombinant retroviral vector as claimed in claim 4 under suitable conditions to allow expression in the cell of the exogenous gene and murine M1/69-J11d heat stable antigen and, identifying the cell and progeny thereof expressing the exogenous gene by detecting cells expressing murine M1/69-J11d heat stable antigen.

7. A method as claimed in claim 6 which further comprises isolating cells and progeny thereof expressing the murine M1/69-J11d heat stable antigen; transplanting the isolated cells into a host; and, monitoring the cells and progeny thereof after transplantation by removing a sample from the host and assaying for cells in the sample expressing the murine M1/69-J11d heat stable antigen.

8. A method of marking a hemopoietic cell and progeny thereof comprising introducing in vitro into a hemopoietic cell of a mammal a recombinant retroviral vector comprising a nucleic acid molecule having a sequence encoding a protein which is not native to the mammal and having the nucleotide sequence of CD24 as shown in the Sequence Listing as SEQ ID No:1 or having a nucleotide sequence encoding the murine M1/69-J11d heat stable antigen as shown in the Sequence Listing as SEQ ID NO:2 under suitable conditions to allow expression of the protein on the surface of the hemopoietic cell or progeny thereof.

9. A method of marking a hemopoietic cell and progeny thereof as claimed in claim 8 wherein the recombinant retroviral vector is Jzen1.

10. A method of marking a hemopoietic cell and progeny thereof as claimed in claim 9 wherein the recombinant retroviral vector is JzenCD24 tKneO.

* * * * *